(12) United States Patent
Yuan et al.

(10) Patent No.: US 6,177,259 B1
(45) Date of Patent: Jan. 23, 2001

(54) ASSAYS AND KITS FOR INHIBITION OF POLYGLUTAMINE-INDUCED CELL DEATH

(75) Inventors: Junying Yuan, Newton; Ivelisse Sanchez, Watertown, both of MA (US)

(73) Assignee: President and Fellows of Harvard College, Cambridge, MA (US)

( * ) Notice: Under 35 U.S.C. 154(b), the term of this patent shall be extended for 0 days.

(21) Appl. No.: 09/368,540

(22) Filed: Aug. 5, 1999

Related U.S. Application Data

(60) Provisional application No. 60/095,640, filed on Aug. 7, 1998.

(51) Int. Cl.[7] .............................. C12Q 1/37; C12Q 1/00; C12N 9/00
(52) U.S. Cl. .................................. 435/23; 435/4; 435/183
(58) Field of Search .................................. 435/4, 23, 183

(56) References Cited

PUBLICATIONS

Wellington et al., J. Biol. Chem. 273: 9158–9167, 1998, Caspase cleavage of gene products associated with triplet expansion disorders generates truncated fragments containing the polyglutamine tract.*

Muzio et al., Cell 85: 817–827, 1996, FLICE, a novel FADD–homologous ICE/CED–3–like protease is recruited to the CD95 (Fas?APO–1) death–inducing signaling complex.*

Alnemri et al., Cell 87: 171, 1996, Human ICE/CED–3 protease nomenclature.*

Martindale et al., Nature Genetics 18: 150–154, 1998, Length of huntingtin and its polyglutamine tract influences localization and frequency of intracellular aggregates.*

Santoro et al., J. Biol. Chem. 273: 13119–13128, 1998, Regulation of protein phosphatase 2A activity by caspase–3 during apoptosis.*

Ikeda et al., Nature Genetics 13: 196–202, 1996, Expanded polyglutamin in the Machado–Joseph disease protein induces cell death in vitro and in vivo.*

* cited by examiner

*Primary Examiner*—Robert A. Schwartzman
*Assistant Examiner*—Andrea Ousley
(74) *Attorney, Agent, or Firm*—Banner & Witcoff, Ltd.

(57) ABSTRACT

The invention provides a method of screening for an inhibitor of cell death, comprising an assay comprising the steps of incubating a first protein comprising a caspase, a second protein comprising a polyglutamine stretch and a candidate inhibitor of cell death under conditions sufficient to permit the formation of a complex comprising the first protein and the second protein, and performing a detection step to detect the formation of a complex, wherein a reduction in the formation of a complex in comparison to that observed when the first and second proteins are incubated in the absence of the candidate inhibitor indicates that the candidate inhibitor is an inhibitor of cell death. A further aspect of the invention is a kit with which to perform this method.

23 Claims, 7 Drawing Sheets

Figure 1A:
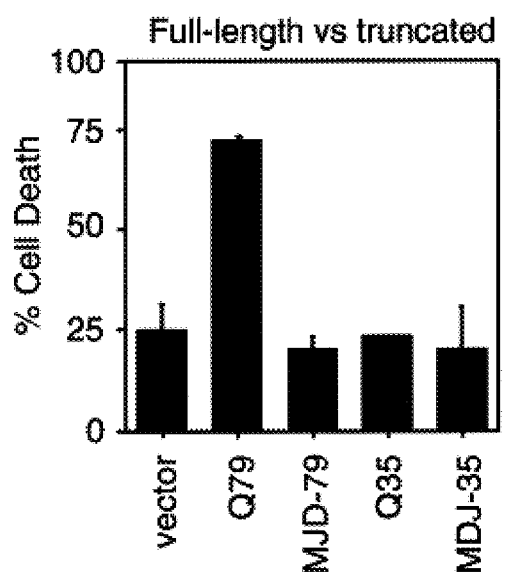

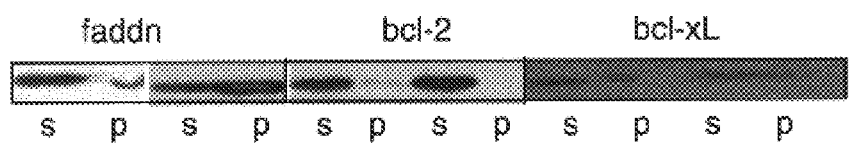
FIG. 3A
FIG. 3B
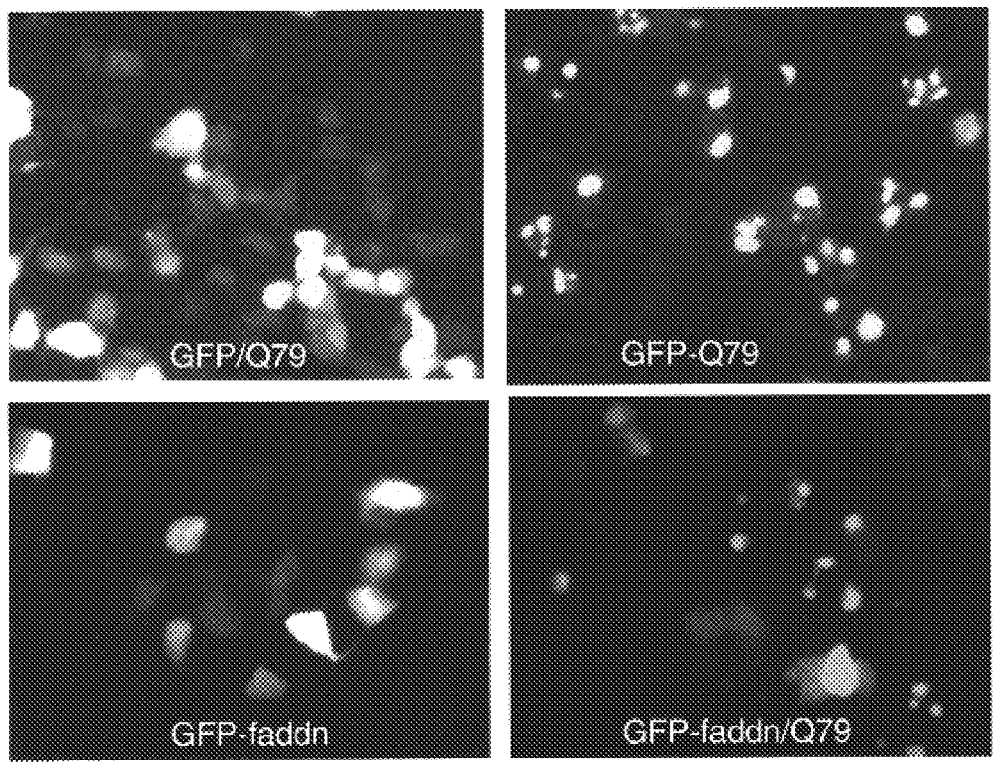
FIG. 3C

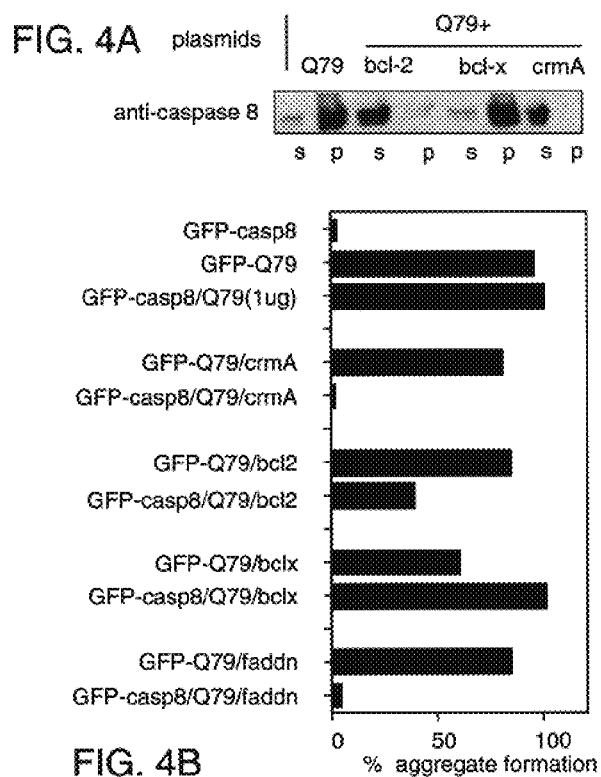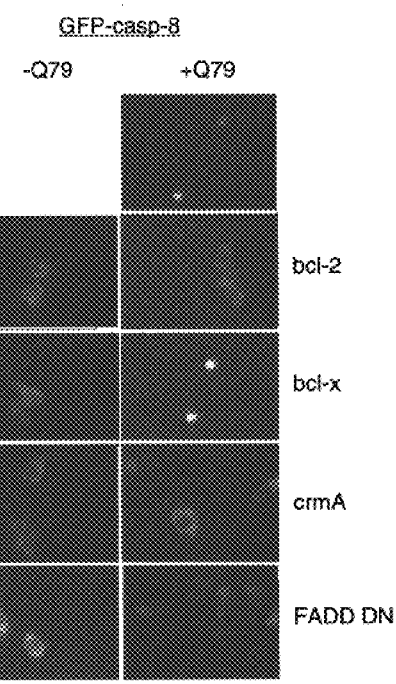
FIG. 4A
FIG. 4B
FIG. 4C

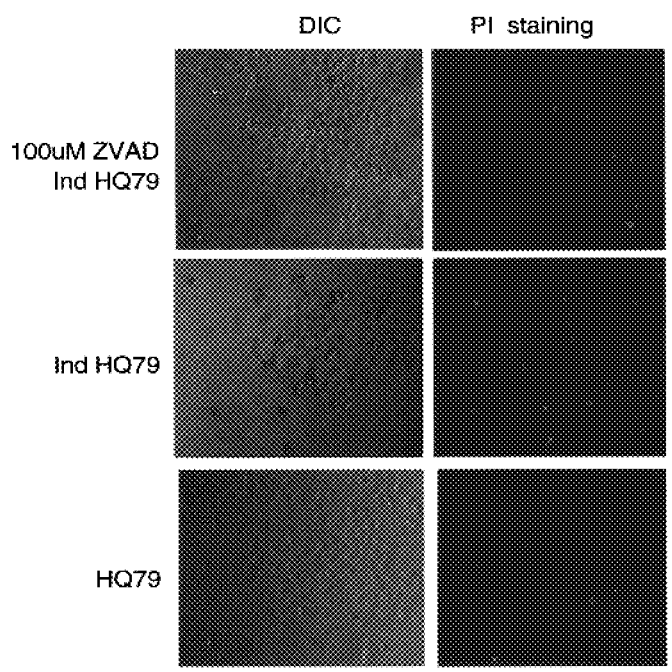
FIG. 6A
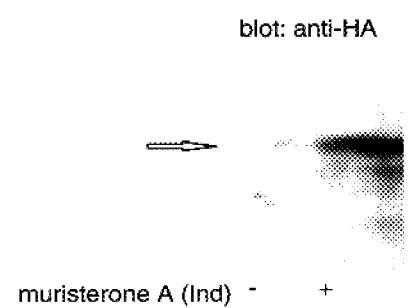
FIG. 6B
FIG. 6C

ASSAYS AND KITS FOR INHIBITION OF POLYGLUTAMINE-INDUCED CELL DEATH

This application claims benefit of Provisional application No. 60/095,640 filed Aug. 7. 1998.

FIELD OF THE INVENTION

The invention relates in general to the screening of candidate pharmacological compositions.

BACKGROUND OF THE INVENTION

Expanded tracts of CAG trinucleotide repeats, encoding polyglutamine, are now known to be the cause of several neurodegenerative diseases, among which are Huntington's Disease (HD; Huntington's Disease Collaborative Research Group, 1993, *Cell,* 72: 971–983) and several types of ataxia, including spinal and bulbar muscular atrophy (La Spada et al., 1991, *Nature Genetics,* 6: 14–18), dentatorubral-pallidoluysian atrophy (Koide, 1994, *Nature Genetics,* 6: 9–13; Nagafachi et al., 1994, *Nature Genetics,* 6: 14–18), and five dominantly inherited ataxias-spinocerebellar ataxia (SCA) types 1–3 (Imbert et al., 1996, *Nature Genetics,* 14: 285–291; Kawaguchi et al., 1994, *Nature Genetics,* 8: 221–228; Orr et al., 1993, *Nature Genetics,* 4: 221–226; Pulst et al., 1996, *Nature Genetics,* 14: 269–276; Sanpei et al., 1996, *Nature Genetics,* 14: 277–284), 6 (Zhuchenko et al., 1997, *Nature Genetics,* 15: 62–69) and 7 (David et al., 1997, *Nature Genetics,* 17: 65–70). These devastating autosomal dominant inherited disorders are characterized by impaired motor control and, in some cases, varying degrees of psychatric and cognitive deficiency (Huntington G., 1872, "On chorea", *Med. Surg. Rep.,* 26: 317–321). Expansion of the glutamine-encoding sequence appears to result in a toxic gain of function that is selectively deleterious to the neurons affected in these diseases (Paulson and Fischbeck, 1996, *Ann Rev. Neurosci.,* 19: 79–107). The genes which are linked to the risk of such neurological disease encode proteins that share no significant sequence homology with each other with the exception of the abnormally long polyglutamine regions.

Expression of truncated cDNAs encoding mostly expanded CAG repeats has been shown to induce cell death, but this effect is not seen when full-length proteins comprising the repeats are produced (Davies et al., 1997, *Cell,* 90: 537–548; Ikeda et al., 1996, *Nature Genetics,* 13: 196–202); therefore, it has been hypothesized that a truncated protein fragment derived from the full-length proteins in each of these disorders may be responsible for the as yet unidentified toxic gain of function leading to the degeneration of different neuronal populations characteristic of each disorder.

Defects in the gene encoding the protein Huntingtin are linked to the development of HD.

Expression of an allele of exon 1 of this gene, which allele contained greater than 21 CAG repeats, has been found to be sufficient to induce pathogenesis and clinical symptoms resembling those of HD in transgenic mice (Bates and Davies, 1997, *Mol. Med. Today,* 3: 508–515). The proteins with expanded polyglutamine repeats have been observed to form aggregates or cytoplasmic and nuclear inclusions in cultured cells overexpressing a truncated MJD protein with an expanded polyglutamine (Ikeda et al., 1996, supra), in transgenic mice expressing a truncated Huntingtin (Bates and Davies, 1997, supra), Drosophila expressing a truncated human ataxin-3 (Warrick et al., 1998, *Cell,* 93: 939–949), and in postmortem SCA 3 patient brain (Paulson et al., 1997, *Neuron,* 19: 333–344); in non-human models, such aggregates and inclusions resemble those observed in sectioned brain tissue derived from affected humans. It has been proposed that such abnormal inclusions may engage in inappropriate protein-protein interactions which lead to cell death. Neither the timing of formation of such inclusions (i.e., whether it preceeds or follows induction of the death program) nor the nature of any causal role for these structures in neurotoxicity has as yet been determined.

There is need in the art for methods and reagents directed at the inhibition of polyglutamine-mediated cell death.

SUMMARY OF THE INVENTION

The invention provides a method of screening for an inhibitor of cell death, comprising an assay comprising the steps of incubating a first protein comprising a caspase, a second protein comprising a polyglutamine stretch and a candidate inhibitor of cell death under conditions sufficient to permit the formation of a complex comprising the first protein and the second protein, and performing a detection step to detect the formation of a complex, wherein a reduction in the formation of a complex in comparison to that observed when the first and second proteins are incubated in the absence of the candidate inhibitor indicates that the candidate inhibitor is an inhibitor of cell death.

As used herein in reference to cell death, the term "inhibitor" refers to an agent which is effective to mediate a reduction in the rate of polyglutamine-inclusion-induced cell death. The efficacy of a candidate inhibitor screened according to the invention may be judged by direct observation of cell survival or, alternatively, of the recruitment of a caspase to a polyglutamine molecule, aggregate or inclusion within a tissue, cell or cell-free assay system of the invention or disruption of protein:protein binding.

As used herein in reference to the action of an inhibitor identified according to the invention, the term "reduction" refers to a decrease of at least 10%, preferably 20–50%, more preferably 75–90% and, most preferably, 95–100% in the mortality of cells having polyglutamine inclusions or aggregates or in the recruitment of a caspase to polyglutamine molecules, inclusions or aggregates.

As used herein with regard to an inhibitor of cell death, the term "candidate" refers to an agent which is assayed according to the invention for efficacy in inhibiting polyglutamine-inclusion-induced cell death; such an agent may be a protein, nucleic acid or other substance, organic or inorganic, as described hereinbelow.

As used herein, the term "caspase" refers to a protein of the caspase protein family including, but not limited to, caspases 1, 2, 3, 4, 5, 6, 7, 8, 9, 10, 11 and 12, proteins which encompass the sequence of—or are substantially similar (e.g. $\geq 50\%$ identical in amino acid sequence) to a caspase protein family member or a peptide fragment thereof which comprises sequence of such a protein. A caspase of the invention may be mutant or wild-type, and may additionally be a recombinant protein, including a fusion protein.

As used herein, the term "polyglutamine stretch" refers to an amino acid sequence which is not normally present in a protein, and comprising a repeated (or expanded) number of glutamine residues. Such a stretch may comprise all or part of a protein, peptide or fragment thereof and, as described below, occurs in many different proteins. A polyglutamine stretch is defined as comprising 36 or more glutamine residues; typically, polyglutamine sequences associated with cell death are at least 36, and preferably more, such as 36, 46, 56, 66, 79, 109, 218, 436 or even up to 1000 glutamine residues in length. A particularly preferred polyglutamine of use in the assays of the invention comprises 79 glutamine residues; it is herein referred to as glutamine$_{79}$ or Q79.

Preferably, the protein comprising a caspase is selected from the group that includes caspases 1,2,3,4,5,6,7,8,9,10,11 and 12.

It is preferred that the polyglutamine repeat is glutamine$_{79}$ (Q79).

In another preferred embodiment, in the step of incubating the first and second proteins, an adaptor protein is incubated with the first and second proteins.

As used herein, the term "adaptor protein" refers to a protein which permits binding of a first and second protein, either by modifying or interacting with (e.g., binding) the first or second protein such that it is then able to bind the other directly, or by binding both of the first and second proteins, thereby creating a bridge such that the first and second proteins are present in the same protein complex but do not contact each other directly.

Preferably, the adaptor protein comprises a death domain (DD) and one of a death effector domain (DED) and a caspase-recruitment domain (CASP).

As used herein, the term "death domain" refers to an amino acid sequence comprising approximately 80 amino acids arranged in six antiparallel, amphipathic helices tightly arranged around a hydrophobic core, which sequence is substantially homologous to the death domain of FADD, which extends from amino acids 101 through 170 (Chinnaiyan et al., 1995, infra) of Genbank accession number U24231.

As used herein, the term "death effector domain" refers to an amino acid sequence comprising approximately 80 amino acids arranged in six antiparallel, amphipathic helices tightly arranged around a hydrophobic core, which sequence is substantially homologous to the death effector domain of FADD, which extends from amino acids 1 through 82 of Genbank accession number U24231 (Eberstadt et al., 1998, infra).

As used herein, the term "caspase-recruitment domain" refers to an amino acid sequence comprising approximately 80 amino acids arranged in six antiparallel, amphipathic helices tightly arranged around a hydrophobic core, which sequence is substantially homologous to the caspase-recruitment domain of caspase-9, which extends from amino acids 1 through 80 of Genbank accession number U60521.

As used herein with regard to the terms "death domain", "death effector domain" and "caspase-recruitment domain", the term "substantially homologous" refers to a protein which is at least 50%, and preferably 70–100% identical in amino acid sequence to that same domain in a second protein.

It is particularly preferred that the adaptor protein is FADD.

Preferably, the detection step comprises the isolation of a complex comprising a first protein and a second protein.

In other preferred embodiments, the detection step comprises the observation of a complex comprising a first protein and a second protein using fluorescent resonance energy transfer (FRET), use of a multiple-hybrid reporter system in yeast, histological examination of cells for signs of cell death, which signs preferably are selected from the group which includes inflation of the nucleus or mitochondria, degradation of chromosomal DNA and rupture of one or more of the nuclear, plasma and mitochondrial membranes.

Preferably, the detection step comprises measuring the survival rate of cells in vivo.

As used herein, the term "survival rate" refers to the percentage of cells in a screening assay system of the invention which remain alive throughout the course of that assay.

It is preferred that the detection step comprises measuring the survival rate of cells in vitro, and more preferred that the cells in vitro are selected from the group that includes mammalian cells and yeast and most preferred that the mammalian cells are neuronal.

Preferably, the cells in vitro comprise one or more of a nucleic acid encoding the first protein, a nucleic acid encoding the second protein and a nucleic acid encoding the candidate inhibitor.

The invention additionally encompasses a kit for identifying an inhibitor of cell death, comprising a first protein comprising a caspase, a second protein comprising a polyglutamine stretch and packaging therefor.

Preferably, the kit further comprises an adaptor protein, more preferably, the adaptor protein comprises a death domain (DD) and one of a death effector domain (DED) and a caspase-recruitment domain (CASP) and, most preferably, the adaptor protein is FADD.

Preferably, the kit further comprises cells.

It is preferred that the cells are selected from the group that includes mammalian cells and yeast.

It is additionally preferred that the cells contain one or more of a nucleic acid encoding the first protein, a nucleic acid encoding the second protein and a nucleic acid encoding a candidate inhibitor of cell death.

Other features and advantages of the invention will be apparent from the following description of the preferred embodiments thereof and from the claims.

BRIEF DESCRIPTIONS OF THE DRAWINGS

Figure 1B:
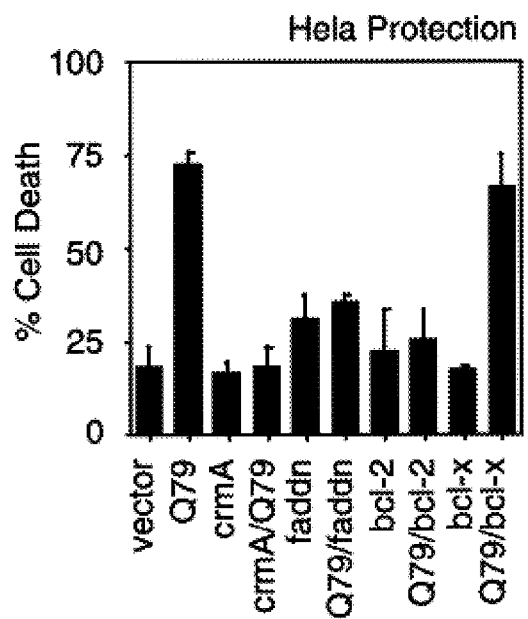
Figure 1C:
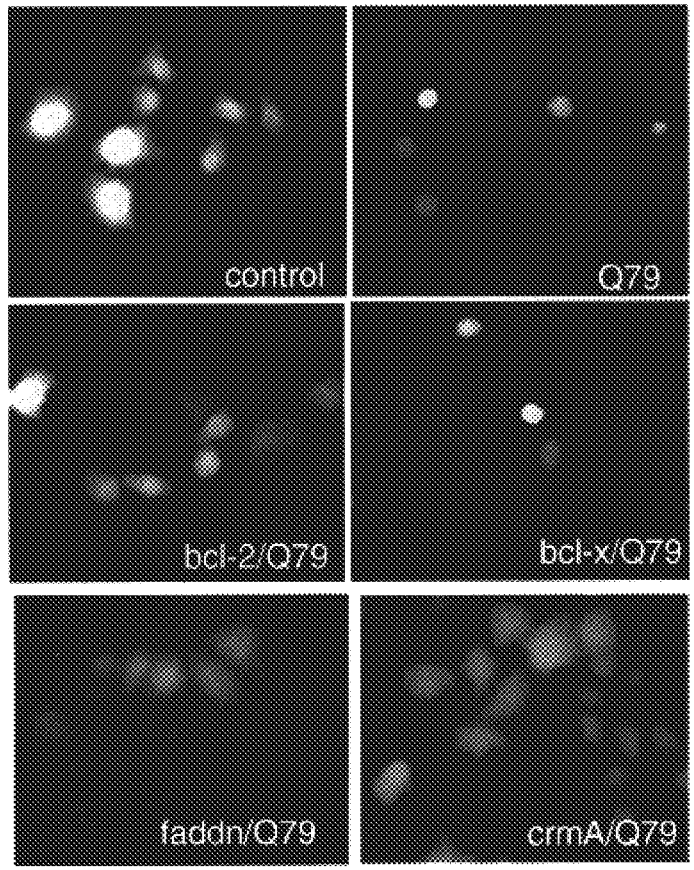

FIGS. 1A, 1B and 1C show the prevention of Q79-induced cell death by crmA, FADD ΔN and Bcl-2. FIG. 1A: Expression of a truncated Q79, but not full length ataxin-3 with 79 glutamine residues (MJD-79) or 35 glutamine residues (MDJ-35) or a truncated Q35, induced HeLa cells to die. FIG. 1B: Co-expression of crmA, FADD ΔN, bcl-2 but not N-terminally tagged Bcl-xL, with Q79 prevented cell death induced by Q79. FIG. 1C: Photomicrographs of HeLa cells transfected with GFP alone (control), GFP and Q79 (Q79), GFP, bcl-2 and Q79 (bcl-2/Q79), GFP, bcl-xL and Q79 (bcl-x/Q79), GFP, FADD ΔN and Q79 (faddn/Q79) and GFP, crmA and Q79 (crmA/Q79).

Figure 2A:
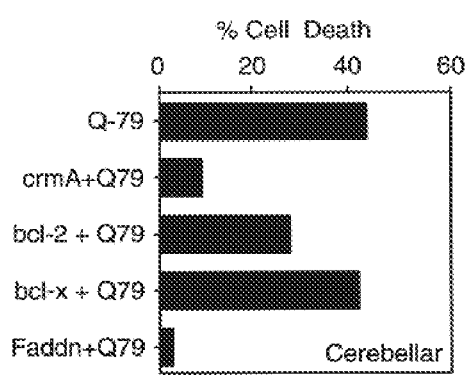
Figure 2B:
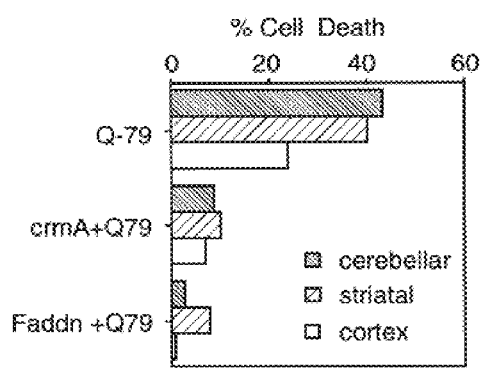
Figure 2C:
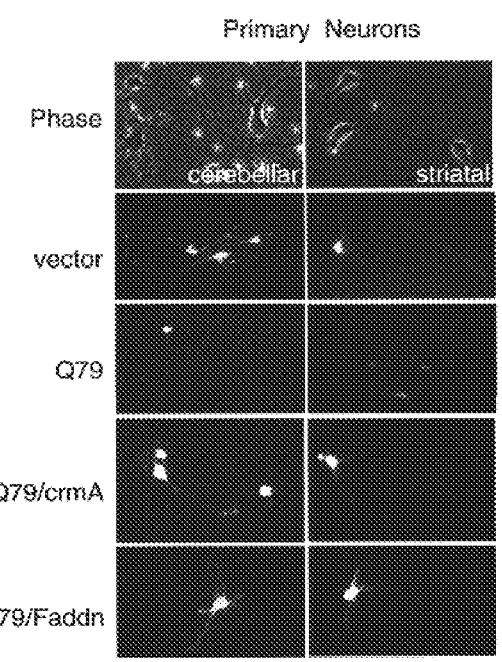

FIGS. 2A, 2B and 2C show the prevention of neuronal cell death induced by Q79. FIG. 2A: Rat primary cerebellar neurons were transfected with Q79 alone, Q79 and crmA, Q79 and bcl-2, Q79 and N-terminally tagged bcl-xL and Q79 and FADD ΔN. Coexpression of crmA, FADD ΔN, bcl-2 but not N-terminally tagged bcl-xL prevented cerebellar neuronal cell death induced by Q79. FIG. 2B: Rat primary cerebellar, striatal and cortical neurons were transfected with Q79 alone, crmA and Q79 and FADD ΔN and Q79. Coexpression of crmA and FADD ΔN prevented neuronal cell death induced by Q79. FIG. 2C: Photomicrographs of rat primary cerebellar and striatal neurons expressing control (GFP vector alone), Q79 and GFP (Q79), Q79, crmA and GFP (Q79/crmA) and Q79, FADD ΔN and GFP (Q79/Faddn).

FIGS. 3A and 3B that FADD ΔN, but not bcl-2, was recruited into insoluble fraction by Q79. FIG. 3A: Western blots of soluble and insoluble cell lysates transfected with Q79, FADD ΔN, Bcl-2 and N-terminally tagged Bcl-xL. FADD ΔN but not bcl-2 is recruited into insoluble fractions in cells expressing Q79. FIG. 3B: HeLa cells expressing GFP and Q79 (GFP/Q79), a GFP-tagged Q79 (GFP-Q79), a GFP-tagged FADD ΔN (GFP-Faddn) and GFP-FADD ΔN and Q79 (GFP-Faddn/Q79). FADD ΔN is recruited into inclusions in cells expressing GFP-FADD ΔN and Q79.

FIGS. 4A, 4B and 4C present recruitment of caspase-8 into insoluble fractions by expression of Q79. FIG. 4A: A western blot of soluble (s) and insoluble (p) fractions of cell lysates expressing Q79 alone (Q79), Q79 and bcl-2 (bcl-2), Q79 and bcl-xL (bcl-x), Q79 and crmA (crmA) probed with caspase-8 antibody. FIG. 4B: Photomicrographs of cells transfected with GFP-caspase in the presence or absence of Q79 plus different inhibitors of apoptosis, bcl-2, N-terminally tagged bcl-xL, crmA and FADD ΔN. FIG. 4C: Percentages of aggregate formation in cells expressing GFP-caspase-8 plus or minus Q79 in the presence of various inhibitors of apoptosis as in B.

Figure 5:
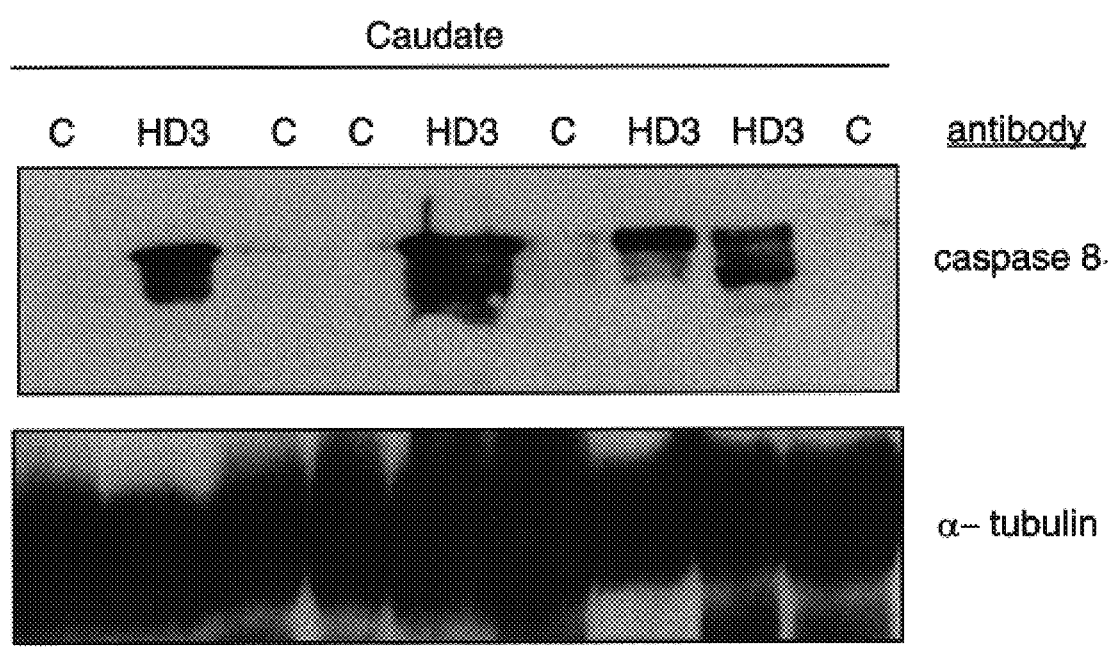

FIG. 5 presents recruitment and activation of caspase-8 in human HD caudate samples. The insoluble fractions of HD and control caudates were subjected to western blot analysis and a strong immunoreactivity was detected in HD caudate samples which corresponds to the molecular weight of activated caspase-8. α-tubulin antibody was used as a control for the amount of protein loaded in each lane.

FIGS. 6A, 6B and 6C Polyglutamine-induced cell death after induction of expanded polyglutamine-repeat. Hela cells stably expressing an inducible construct encoding a polyglutamine stretch of 79 residues tagged with HA (HQ79) and the ecdyosone receptor pVgRxR are described. Panels on the left show differential interference contrast (DIC) microscopy and propidium iodine (PI) fluorescence of Hela cells (left and right panel, respectively). 6A) Hela cells induced to express Q79 in the presence or absence of 100 uM ZVAD (Top and middle panels). Uninduced Hela cells (bottom panels). 6B)-Quantitation of propidium iodine positive cells as measure of cell death 48 hours after induction of HA-Q79 expression. 6C) Induction of Q79 expression with muristerone A. Immunoblots of lysates from uninduced (−) and induced (+) HQ79 Hela cells with anti-HA antibody. The HA tagged Q79 protein can be detected in lysates from induced but not in the uninduced cells (arrow).

Figure 7:
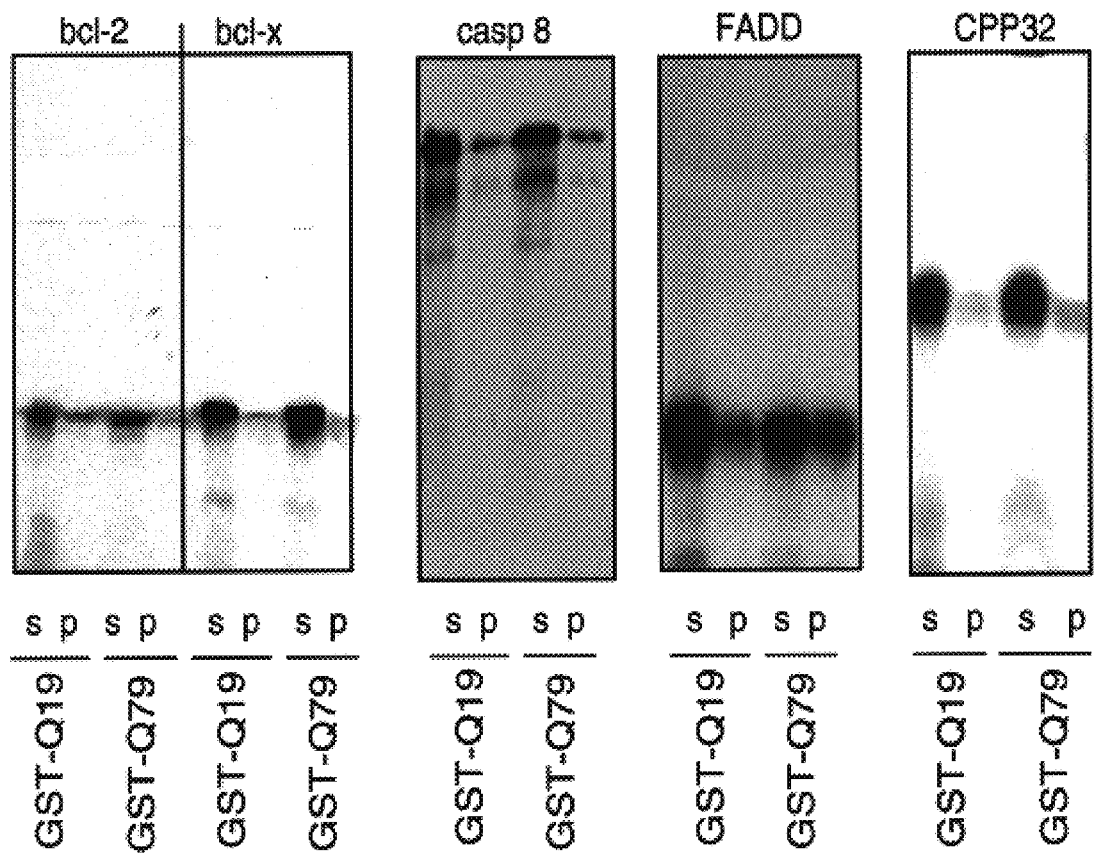

FIG. 7 In vitro binding assays of expanded polyglutamine repeats. Constructs encoding a GST fusion to a truncated form of DRPLA consisting mostly of a 19 or 81 polyglutamine stretch were expressed in bacteria. The GST fusion protein was purified using glutathione beads (Pharmacia, Co) was incubated with in vitro translated $S^{35}$ labelled protein (Promega,Co) in the presence of binding buffer; 250 mM NaCl, 1%NP-40, 1 mM EDTA, and 1 mM DTT. The glutathione-beads were removed by brief centrifugation and the remaining supernate was removed. The glutathione beads were washed several times in binding buffer. The supernate and bead pellet samples loaded onto 15% SDS-PAGE gels. Constructs used included human N-tagged Bcl-x and Bcl-2, caspase 8, FADD, and Caspase 3 (CPP32). FADD, but not CPP32, Bcl-x, Bcl-2, or caspase 8, appear to preferentially bind expanded- polyglutamine stretches (Q81).

DESCRIPTION OF THE INVENTION

The invention is based upon the discovery that a caspase protein is recruited to polyglutamine aggregates in neuronal cells, and that this recruitment is an essential element of a pathway leading to the death of these cells.

The relationship between proteins or protein fragments containing expanded polyglutamine sequences and neuropathology is well established, as described above. The invention represents the first realization that a caspase associates with a protein containing a polyglutamine stretch, and the first association of a caspase with polyglutamine-associated cell death. The invention therefore provides a target (namely, the caspase:polyglutamine complex) at which therapeutic strategies may be aimed and further provides a powerful means by which to perform the screening of compounds which may enhance neuronal cell survival by inhibiting the association of a caspase with a polyglutamine molecule, aggregate or inclusion.

Polyglutamine Molecules in the Invention

As described hereinabove, the expansion of nucleic acid sequences comprising strings of repeated CAG motifs is known to be linked with the etiology of several neuropathological states and it is hypothesized that events associated with the aggregation of protein fragments containing abnormally long polyglycine repeats trigger the entry of a susceptible neuron into a pathway of programmed cell death. Polyglutamine stretches comprising at least 36, but commonly 79, amino acids have been associated with disease states.

Caspases

Caspases are believed to be responsible for the cleavage of mutant proteins containing expanded polyglutamine tracts and for the generation of toxic protein fragments in vitro and in culture systems (Goldberg et al., 1996, *Nature Genetics*, 13: 442–449; Miyashita et al., 1997, *J. Biol. Chem.*, 272: 29238–29242; Wellington et al., 1998, *J. Biol. Chem.*, 273: 9158–9167); however, a critical role of caspases in generating toxic protein fragments in vivo and a possible role of caspases after the initial cleavage event have not yet been demonstrated. At present and herein defined, the "caspase family" is known to comprise 12 members, caspases 1, 2, 3, 4, 5, 6, 7, 8, 9, 10, 11 and 12 (as reviewed by Cryns and Yuan, 1998, supra); one of these, caspase 9, is described as comprising the prototype caspase-recruitment domain (CARD), and thus the term "caspase" refers to any of caspases 1 through 12. Mammalian caspases are homologues of the product of the *C. elegans* cell-death gene ced-3 and have been shown to play important roles in regulating apoptosis (Cryns and Yuan, 1998, supra). A cowpox virus cytokine response modifier gene (crmA) encodes a serpin that is a specific inhibitor of two mammalian caspases, caspase-1 and caspase-8 (Zhou et al., 1997, *J. Biol. Chem.*, 272: 7797–7800). Apoptosis is a genetically regulated cellular suicide mechanism which is responsible for regulating cell numbers during development and in defense of homeostasis (Cryns and Yuan, 1998, *Genes Dev.*, 12: 1551–1570). Abnormal apoptosis contributes to a variety of human disorders including cancer and acute and chronic neuronal degenerative disorders. Mammalian apoptosis is regulated by an evolutionarily conserved pathway(s) whose critical gene products are homologues of *C. elegans* programmed cell death pathway (Cryns and Yuan, 1998, supra). The Bcl-2 family of proteins are mammalian homologues of *C. elegans* cell death suppressor Ced-9. Expression of Bcl-2 and Bcl-xL, two major anti-apoptotic members of the family, inhibits apoptosis in a variety of cell types (Merry and Korsmeyer, 1997, *Ann. Rev. Neurosci*, 20: 245–267).

The Fas pathway of apoptosis has been shown to play an important role in immune systems and involved in cytotoxic T cell (CTL) mediated cytotoxicity and down regulation of immune responses (Nagata and Golstein, 1995, *Science*, 267: 1449–1456). Activation of the Fas pathway by Fas ligand or agonistic antibodies induces oligomerization of Fas receptor which exposes its intracellular protein-protein interacting domain, termed death domain (DD), resulting in the formation of the death-inducing signaling complex which transduces the Fas death signal (Kischkel et al., 1995, *EMBO. J.,* 14: 5579–5588). In the DISC, the DD of Fas receptor interacts and recruits FADD (Fas/APO-1-associated death domain protein), an adaptor protein containing a death domain at its C-terminal half and another protein-protein interacting domain, termed death effector domain (DED), at its N-terminal half (Chinnaiyan et al., 1995, *Cell,* 81: 505–512). FADD in turn recruits caspase-8 which contains two death effector domains at its N-terminal half and a caspase domain at its C-terminal half. Expression of a truncated FADD (FADD ΔN) containing the C-terminal death domain only inhibits Fas-induced cell death (Chinnaiyan et al., 1996, *J. Biol. Chem.,* 271: 4961–4965). NMR structure analyses of the death domain and death effector domain have shown that these two protein-protein interacting domains consist of antiparallel, amphipathic α-helices that are similar in their overall three dimensional structures (Eberstadt et al., 1998, *Nature,* 392: 941–945; Huang et al., 1996, *Nature,* 384: 638–641).

Since caspases play an important role in regulating mammalian apoptosis, we determined the involvement of caspases in the polyglutamine induced cell death. We report here that caspase-8 is recruited by inclusions of expanded polyglutamine repeats in cultured cells and primary neurons and inhibition of caspase-8 recruitment inhibits the cell death induced by expanded polyglutamine repeats.

A. Screening Systems According to the Invention

A minimal system in which to test the inhibition of cell death according to the invention comprises a caspase and a polyglutamine molecule. Such a kit may additionally include an adaptor protein or other molecule (including, but not limited to, FADD) through which a caspase associates with a polyglutamine molecule. A useful adaptor molecule typically comprises a death domain and one of a death effector domain and a caspase-recruitment domain. Such a system may be cell-free, or may comprise cells. In the latter case, a candidate inhibitor of cell death may be administered to cells comprising a caspase and a polyglutamine molecule either in vitro or in vivo. Non-limiting examples of in vitro and in vivo test systems are described below.

Cell-Free Assay Systems of the Invention

A cell-free assay system according to the invention is required to permit the protein:protein interaction of interest to occur in the absence of a candidate inhibitor. Such a system may comprise a low-ionic-strength buffer (e.g., physiological salt, such as simple saline or phosphate- and/or Tris-buffered saline, a cell culture medium, of which many are known in the art, or a whole or fractionated cell lysate. The caspase and polyglutamine molecules, as well as a candidate inhibitor, may be added into a buffer, medium or lysate or may have been expressed in cells from which a lysate is derived. Alternatively, a cell-free transcription- and/or translation system may be used to deliver one or more of these components, if it is so desired, to the assay system.

An assay of the invention may be performed in a standard in vitro transcription/translation system under conditions which permit expression of a recombinant or other gene. The TnT® T7 Quick Coupled Transcription/Translation System (Cat. # L1170; Promega) contains all reagents necessary for in vitro transcription/translation except the DNA of interest and the detection label. The TnT® Coupled Reticulocyte Lysate Systems (comprising a rabbit reticulocyte lysate) include: TnT® T3 Coupled Reticulocyte Lysate System (Cat. # L4950; Promega); TnT® T7 Coupled Reticulocyte Lysate System (Cat. # L4610; Promega); TnT® SP6 Coupled Reticulocyte Lysate System (Cat. # L4600; Promega); TnT(® T7/SP6 Coupled Reticulocyte Lysate System (Cat. # L5020; Promega); TnT® T7/T3 Coupled Reticulocyte Lysate System (Cat. # L5010; Promega).

An assay involving a cell lysate or a whole cell may be performed in a cell lysate or whole cell preferably eukaryotic in nature (e.g., yeast, fungi, insect (e.g., Drosophila), mouse, or human). An assay in which a cell lysate is used is performed in a standard in vitro system under conditions which permit gene expression. A rabbit reticulocyte lysate alone is also available from Promega, either nuclease-treated (Cat. # L4960) or untreated (Cat. # L4151). An assay in which a whole cell is used is described in detail below.

In Vitro Cellular Assay Systems of the Invention i. Cells Useful in Screening Assays of the Invention When performed in vitro in an assay system using cells, the methods of the invention are broadly applicable to a host cell susceptible to transfection or transformation, such as bacteria (both gram-positive and gram-negative), cultured- or explanted vertebrate cells (e.g., mammalian stem cells) and yeast.

Organisms are currently being developed for the expression of therapeutic or prophylatic agents including DNA, RNA, proteins, non-proteinaceous compounds, and viruses. Such vector microorganisms include bacteria such as Clostridium (Parker et al., 1947, *Proc. Soc. Exp. Biol. Med.,* 66: 461–465; Fox et al., 1996, *Gene Therapy, b 3: 173–178;* Minton et al., 1995, *FEMS Microbiol. Rev.,* 17: 357–364), Salmonella (Pawelek et al., 1997, *Cancer Res.,* 57: 4537–4544; Saltzman et al., 1996, *Cancer Biother, Radiopharm.,* 11: 145–153; Carrier et al., 1992,*J. Immunol.,* 148: 1176–1181; Su et al., 1992, *Microbiol. Pathol.,* 13: 465–476; Chabalgoity et al., 1996, *Infect. Immunol.,* 65: 2402–2412), listeria (Schafer et al., 1992,*J. Immunol.,* 149: 53–59; Pan et al., 1995, *Nature Med.,* 1: 471–477) and Shigella (Sizemore et al., 1995, *Science,* 270: 299–302), as well as yeast, mycobacteria, slime molds (members of the taxa Dictyosteliida—such as of the genera Polysphondylium and Dictystelium, e.g. *Dictyostelium discoideum*—and Myxomycetes—e.g. of the genera Physarum and Didymium) and members of the Domain Arachaea (including, but not limited to, archaebacteria), which have begun to be used in recombinant nucleic acid work, members of the phylum Protista, or other cell of the algae, fungi, or any cell of the animal or plant kingdoms.

Mammalian cells are of use in the invention. Such cells include, but are not limited to, neuronal cells (those of both primary explants and of established cell culture lines) cells of the immune system (such as T-cells, B-cells and macrophages), fibroblasts, hematopoietic cells and dendritic cells. Using established technologies, stem cells (e.g. hematopoietic stem cells) may be used for gene transfer after enrichment procedures. Alternatively, unseparated hematopoietic cells and stem cell populations may be made susceptible to DNA uptake. The use of neuronal cells according to the invention is demonstrated in Examples 1 and 2. Transfection of hematopoietic stem cells is described in Mannion-Henderson et al., 1995, *Exp. Hematol.,* 23: 1628; Schiffmann et Schiffmann et al., 1995, *Blood,* 86: 1218; Williams, 1990, *Bone Marrow Transplant,* 5: 141; Boggs, 1990, *Int. J. Cell Cloning,* 8: 80; Martensson et al., 1987, *Eur. J. Immunol.,* 17: 1499; Okabe et al., 1992, *Eur. J.*

*Immunol.,* 22: 37–43; and Baneiji et al., 1983, *Cell,* 33: 729. Such methods may advantageously be used according to the present invention.

ii. Nucleic Acid Vectors for the Expression of Screening Assay Components in Cells A nucleic acid of use according to the methods of the invention may be either double- or single stranded and either naked or associated with protein, carbohydrate, proteoglycan and/or lipid or other molecules. Such vectors may contain modified and/or unmodified nucleotides or ribonucleotides. In the event that the gene to be transfected may be without its native transcriptional regulatory sequences, the vector must provide such sequences to the gene, so that it can be expressed once inside the target cell. Such sequences may direct transcription in a tissue-specific manner, thereby limiting expression of the gene to its target cell population, even if it is taken up by other surrounding cells. Alternatively, such sequences may be general regulators of transcription, such as those that regulate housekeeping genes, which will allow for expression of the transfected gene in more than one cell type; this assumes that the majority of vector molecules will associate preferentially with the cells of the tissue into which they were injected, and that leakage of the vector into other cell types will not be significantly deleterious to the recipient mammal. It is also possible to design a vector that will express the gene of choice in the target cells at a specific time, by using an inducible promoter, which will not direct transcription unless a specific stimulus, such as heat shock, is applied.

A gene encoding a component of the assay system of the invention or a candidate inhibitor of cell death may be transfected into a cell or organism using a viral or non-viral DNA or RNA vector, where non-viral vectors include, but are not limited to, plasmids, linear nucleic acid molecules, artificial chromomosomes and episomal vectors. Expression of heterologous genes in mammals has been observed after injection of plasmid DNA into muscle (Wolff J. A. et al., 1990, *Science,* 247: 1465–1468; Carson D. A. et al., U.S. Pat. No. 5,580,859), thyroid (Sykes et al., 1994, *Human Gene Ther.,* 5: 837–844), melanoma (Vile et al., 1993, *Cancer Res.,* 53: 962–967), skin (Hengge et al., 1995, *Nature Genet.,* 10: 161–166), liver (Hickman et al., 1994, *Human Gene Therapy,* 5: 1477–1483) and after exposure of airway epithelium (Meyer et al., 1995, *Gene Therapy,* 2: 450–460).

In addition to vectors of the broad classes described above and the mammalian gene expression constructs used in Examples 1 and 2, microbial plasmids, such as those of bacteria and yeast, are of use in the invention. Yeast plasmids, which are useful in the screening assays described herein as expression vectors in multiple-hybrid assays of protein interaction, are particularly preferred.

Bacterial Plasmids

Of the frequently used origins of replication, pBR322 is useful according to the invention, and pUC is preferred. Although not preferred, other plasmids which are useful according to the invention are those which require the presence of plasmid encoded proteins for replication, for example, the pT181, FII, and FI origins of replication.

Examples of origins of replication which are useful in assays of the invention in *E. coli* and *S. typhimurium* include but are not limited to, pHETK (Garapin et al., 1981, *Proc. Natl. Acad. Sci. U.S.A.,* 78: 815–819), p279 (Talmadge et al., 1980, *Proc. Natl. Acad. Sci. U.S.A.,* 77: 3369–3373), p5–3 and p21A-2 (both from Pawalek et al., 1997, *Cancer Res.,* 57: 4537–4544), pMB1 (Bolivar et al., 1977, *Gene,* 2: 95–113), ColE1 (Kahn et al., 1979, *Methods Enzymol.,* 68: 268–280), p15A (Chang et al., 1978, *J. Bacteriol.,* 134: 1141–1156); pSC101 (Stoker et al., 1982, *Gene,* 18: 335–341); R6K (Kahn et al., 1979, supra); R1 (temperature dependent origin of replication, Uhlin et al., 1983, *Gene,* 22: 255–265); lambda dv (Jackson et al., 1972, *Proc. Nat. Aca. Sci. U.S.A.,* 69: 2904–2909); pYA (Nakayama et al., 1988, infra). An example of an origin of replication that is useful in Staphylococcus is pT181 (Scott, 1984, *Microbial Review* 48: 1–23). Of the above-described origins of replication, pMB1, p15A and ColE1 are preferred because these origins do not require plasmid-encoded proteins for replication.

Yeast Plasmids

Three Systems Are Used For Recombinant Plasmid Expression And Replication In Yeasts 1. Integrating. An example of such a plasmid is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g. as described by Rose et al., 1990, *Methods in Yeast Genetics,* Cold Spring Harbor Laboratory Press, Cold Spring Harbor, N.Y.). The cells are treated with lithium acetate to achieve transformation efficiencies of approximately $10^4$ colony-forming units (transformed cells)/$\mu$g of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN, of which YCp is an example. Such a plasmid contains the autonomous replicating sequence (ARS 1), a sequence of approximately 700 bp which, when carried on a plasmid, permits its replication in yeast, and a centromeric sequence (CEN4), the latter of which allows mitotic stability. These are usually present at 1–2 copies per cell. Removal of the CEN sequence yields a YRp plasmid, which is typically present in 100–200 copes per cell; however, this plasmid is both mitotically and meiotically unstable.

3. High-copy-number 2p circles. These plasmids contain a sequence approximately 1 kb in length, the $2\mu$ sequence, which acts as a yeast replicon giving rise to higher plasmid copy number; however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

As suggested above, examples of yeast plasmids useful in the invention include the YRp plasmids (based on autonomously-replicating sequences, or ARS) and the YEp plasmids (based on the $2\mu$ circle), of which examples are YEp24 and the YEplac series of plasmids (Gietz and Sugino, 1988, *Gene,* 74: 527–534). (See Sikorski, "Extrachromsomoal cloning vectors of *Saccharomyces cerevisiae*", in *Plasmid, A Practical Approach,* Ed. K. G. Hardy, IRL Press, 1993; and *Yeast Cloning Vectors and Genes, Current Protocols in Molecular Biology,* Section II, Unit 13.4, Eds., Ausubel et al., 1994).

In addition to a yeast origin of replication, yeast plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following (with the gene product listed in parentheses and the sizes quoted encompassing the coding sequence, together with the promoter and terminator elements required for correct expression):

TRP1 Phosphoribosylanthranilate isomerase, which is a component of the tryptophan biosynthetic pathway).

URA43 (Orotidine-5'-phosphate decarboxylase, which takes part in the uracil biosynthetic pathway).

LEU2 (3-Isopropylmalate dehydrogenase, which is involved with the leucine biosynthetic pathway).

HIS3 (Imidazoleglycerolphosphate dehydratase, or IGP dehydratase).

LYS2 (α-aminoadipate-semialdehyde dehydrogenase, part of the lysine biosynthetic pathway).

In Vivo Assay System of the Invention

Alternatively, the screening system may operate in vivo, i.e., in an intact, living multicellular organism, such as an insect or a mammal. For example, mice which are transgenic for gene expression constructs encoding one or more of a protein encompassing a caspase (e.g., one of caspases 1 through 12 or a protein, such as FLIP or FLICE, which comprises a caspase domain), a polyglutamine or an adaptor molecule through which a caspase may associate with polyglutamine and a candidate inhibitor of cell death according to the invention. Methods of generating transgenic Drosophila, mice and other organisms are well known in the art. A candidate inhibitor of cell death is administered (e.g. by feeding or injection) to a test organism (including, but not limited to, a fly or mouse) and protein:protein complex formation or cell death is assayed. After sufficient time has passed to allow for gene expression and inhibition of caspase:polyglutamine binding by the candidate inhibitor, a detection procedure may be performed by a method from the list that includes, but is not limited to, the molecular, biochemical (including enzymatic assay) and histological (including immunohistochemical and enzymatic staining, e.g. using a chromogenic, fluorescent, luminescent or radioactive substrate of caspase) methods described herein.

Candidate Inhibitors According to the Invention

A "candidate inhibitor" as used herein, is any compound with a potential to reduce or block the recruitment of caspase to polyglutamine aggregates or inclusions according to the invention; such inhibition may be direct (e.g. including, but not limited to, cleavage of the caspase:polyglutamine complex or competitive binding of another substance to either of component of the caspase:polyglutamine complex) or indirect (e.g. by blocking the initial production of caspase or of protein fragments encompassing extended polyglutamine stretches).

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (N.C.), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate inhibitors which may be screened according to the methods of the invention include those encoding receptors, enzymes, ligands, regulatory factors, and structural proteins. Candidate inhibitors also include nuclear proteins, cytoplasmic proteins, mitochondrial proteins, secreted proteins, plasmalemma-associated proteins, serum proteins, viral antigens, bacterial antigens, protozoal antigens and parasitic antigens. Candidate inhibitors additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens.

Candidate inhibitors which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate inhibitors described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the a target MRNA. Ribozymes of the hammerhead class are the smallest known, and lend themselves both to in vitro synthesis and delivery to cells (summarized by Sullivan, 1994, *J. Invest. Dermatol.*, 103: 85S–98S; Usman et al., 1996, *Curr. Opin. Struct. Biol.*, 6: 527–533).

B. Determination of the Efficacy of a Candidate Inhibitor of Cell Death According to the Invention Methods of Detecting Protein:Protein Complexes a. Isolation of Protein:Protein Complexes I. Immunoprecipitation Protein:protein complexes comprising a caspase and either a polyglutamine or an adaptor molecule which permits the association of a caspase with polyglutamine can be precipitated from solution (whether from a protein binding buffer or from a cell or tissue lysate, as described above) by antibodies specific for one or the other of the binding partners. As described above, an antibody may be produced by methods well known in the art, if one of the desired specificity is not publicly available (e.g. from a public repository such as the American Type Culture Collection or from a commercial supplier). In order to confirm that both binding partners are present in the precipitate, serial immunoprecipitation may be performed in which proteins are first precipitated through their association with an antibody specific for one binding partner, and then resuspended and precipitated again using an antibody specific for the other. The end-product should be limited to protein:protein complexes having epitopes present on both target proteins. A reduction of at least 30% in the recovery of complexes comprising both a capase and a protein comprising a polyglutamine stretch in immunoprecipitations of samples comprising the inhibitor relative to control samples is indicative of efficacy of the inhibitor according to the invention.

Methods for the preparation of antibodies are well known in the art, and are briefly summarized as follows:

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

1. Polyclonal Antibodies

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.*, 267: 4815–4823). The serum is titered against protein antigen by ELISA (below) or alternatively by dot or spot blotting (Boersma and Van Leeuwen, 1994,*J. Neurosci. Methods,* 51: 317). At the same time, the antiserum may be used in tissue sections prepared as described below. The serum is shown to react strongly with the appropriate peptides by ELISA, for example, following the procedures of Green et al., 1982, *Cell,* 28: 477–487.

2. Monoclonal Antibodies

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., *Nature,* 294, 278–280 (1981).

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

ii. Affinity Purification

As an alternative to precipitation from solution, either an antibody or another protein having affinity for a caspase: (polyglutamine or adaptor) complex may be bound to a solid or semi-solid support (e.g. a membrane, filter or chromatography column resin), which is then incubated with a buffer or lysate derived from cells or tissue, which buffer or lysate comprises the components of the complex either with or without the candidate inhibitor, under conditions which permit formation of the complex in the absence of the candidate inhibitor. A candidate inhibitor is judged to be efficacious if it results in a reduction of at least 30% in the yield of affinity-purified complexes comprising a caspase and a protein comprising a polyglutamine stretch relative to that observed with control purifications in which it is absent.

If a caspase:adaptor complex is to be isolated, polyglutamine may be bound to the support; alternatively, an antibody specific for either caspase or the adaptor may be used.

iii. Additional Use of Crosslinking Agents

In the isolation procedures described above, conditions (e.g., temperature or buffer composition) which favor the dissociation of protein:protein complexes are often required in order to improve yield sufficiently to permit recovery of a rare species or to free hydrophobic proteins from membranous structures. Methods for covalently crosslinking proteins to proteins or other biomolecules with which they may associate intracellularly or in a cell-free assay system are well know in the art. Table 1 provides a non-exhaustive list of chemical crosslinking substances which are widely available, along with their catalog numbers from one commercial supplier (Sigma; St. Louis, Mo.).

| Product Number | Name; synonyms | Type = Homobifunctional < Heterobifunctional Cleavable x | | Specificity Primary Reaction | Secondary Reaction | Linker arm (atoms) | Comments |
|---|---|---|---|---|---|---|---|
| A 1251 | S-Acetylmercaptosuccinic anhydride; SAMSA | < | | amine | maleimide | 3 | Charged; incorporates protected -SH; readily S-deacetylated |
| A 9043 | S-Acetylthioglycolic acid NHS ester; SATA | | | amine | maleimide | 3 | Incorporates protected -SH; readily S-deacetylated |
| A 5261 | S-Acetylthiopropionic acid NHS ester; SAPTA | < | | amine | maleimide | 4 | Incorporates protected -SH; readily S-deacetylated |
| A 0638 | Adipic acid dihydrazide | = | | carbohydrate | | 10 | Reacts with aldehyde of periodate-oxidized carbohydrate |
| A 9048 | 4-Azidobenzoic acid NHS ester; HSAB | < | | amine | photoactive | 6 | Aryl azide photoaffinity reagent |
| A 3282 | N-(5-Azido-2-nitrobenzoyloxy)succmimide | < | | amine | photoactive | 5 | Aryl azide photoaffinity reagent |
| A 3407 | 6-(4-Azido-2-nitrophenylamino)-hexanoic acid NHS ester | < | | amine | photoactive | 11 | Aryl azide photoaffinity reagent |
| A 6057 | p-Azidophenacyl bromide; APB | < | | sulfhydryl | photoactive | 7 | Aryl azide photoaffinity reagent |
| A 3532 | N-(4-Azidophenylthio)phthalimide; APTP | < | | sulfhydryl | photoactive | 6 | Aryl azide photoaffinity reagent |
| A 9173 | 4-Azidosalicylic acid NHS ester | < | | amine | photoactive | 6 | Aryl azide photoaffinity reagent; may be radioiodinated |
| B 4412 | 4-Benzoylbenzoic acid NHS ester | < | | amine | photoactive reagent | 6 | Benzophenone photoaffinity |
| B 8271 | Bromoacetic acid NHS ester | < | | amine | sulfhydryl | 2 | Haloacetyl group reacts preferentially with -SH nucleophile |
| C 1526 | Carbonyl-bis(L-methionine p-nitro-phenyl ester) | = | x | amine | | 7 | Cleavable by cyanogen bromide |
| D 7147 | 2-Diazo-3,3,3-trifluoropropionic acid p-nitrophenyl ester | < | | amine | photoactive | 2 | Diazo photoaffinity reagent; trifluoromethyl group improves stability and efficiency |
| D 5378 | 1,5-Difluoro-2,4-dinitrobenzene; DFNB | = | | amine | | 3 | Aryl halide reaction with nucleophile other than amine is readily reversible |
| D 3514 | 4,4'-Diisothiocyanatostilbene-2,2'-disulfonic acid | = | | amine | | 14 | Negatively charged; specific inhibitor of cellular anion permeability |
| D 0172 | Diethyl malonimidate | = | | amine | | 3 | Water soluble; amidine product is charged; base-labile |
| D 8138 | Dimethyl adipimidate; DMA | = | | amine | | 6 | Water soluble; amidine product is charged; base-labile |
| D 2388 | Dimethyl 3,3'-dithiobispropion-imidate; DTPB | = | | amine | | 8 | Water soluble; amidine product is charged; base labile; cleavable by mercaptan |
| D 8388 | Dimethyl pimelimidate; DMP | = | | amine | | 7 | Water soluble; amidine product is charged; base iabile |
| D 7636 | Dimethyl suberimidate; DMS | = | | amine | | 8 | Water soluble; amidine product is charged; base labile |
| D 7272 | 4,4'-Dithiobis(phenyl azide); DABP | = | x | photoactive | | 12 | Aryl azide photoaffmity reagent; cleavable by mercaptan |
| D 3669 | 3,3'-Dithiobis(propionic acid NHS ester); DTSP; Lomant's Reagent | = | x | amine | | 8 | Cleavable by mercaptan |
| E 3257 | Ethylene glycol bis(succimc acid NHS ester); EGS-NHS | = | x | amine | | 12 | Cleavable by hydroxylamine |
| F 9382 | 4-Fluro-3-nitrophenyl azide; FNA | < | | amine | photoactive | 5 | Aryl azide photoaffinity reagent |
| F 3626 | bis(4-Fluoro-3-nitrophenyl) sulfone | = | x | amine | | 9 | Aryl haiide; cleavable with base |
| F 7640 | p-Formylbenzoic acid NHS ester | < | | amine | amine | 6 | Second reaction requires reductive amination |
| MANY | Glutaraidehyde | = | | amine | | varies | Used for protein conjugation |
| I 6256 | 2-Iminothiolane | < | | amine | maleimide | 5 | Thiolating reagent; amidine product is charged |
| I 1007 | 6-(Iodoacetaniido)caproic acid NHS ester | < | | amine | sulfhydryl | 9 | Haloacetyl group reacts preferentially with sulfhydryl nucleophile |
| I 9760 | Iodoacetic acid NHS ester | < | | amine | sulfhydryl | 2 | Haloacetyl group reacts preferentially with sulfhydryl nucleophile |
| M 3884 | Maleimidoacetic acid NHS ester; AMAS | < | | amine | sulfhydryl | 5 | Used for protein conjugation |
| M 2786 | m-Maleimidobenzoic acid NHS ester; MBS | < | | amine | sulfhydryl | 7 | Used for protein conjugation; aryl maleimide is less stable than alkyl |
| M 9775 | 4-(N-Maieimido) benzophenone | < | | sulfhydryl | photoactive | 8 | Benzophenone photoaffinity product |
| M 7642 | γ-Maleimidobutyric acid NHS ester | < | | amine | sulfhydryl | 7 | Used for protein conjugation |
| M 9794 | ε-Maleimidocaproic acid NHS ester | < | | amine | sulfhydryl | 9 | Used for protein conjugation |

-continued

| Product Number | Name; synonyms | Type: = Homobifunctional, < Heterobifunctional Cleavable, x | Specificity: Primary Reaction | Secondary Reaction | Linker arm (atoms) | Comments |
|---|---|---|---|---|---|---|
| M 5525 | 4-(N-Maieimidomethyl)cyclohexane-carboxylic acid NHS ester; SMCC | < | amine | sulfhydryl | 9 | Used for protein conjugation |
| M 6035 | 4-(N-Maleimidomethyl)cyclohexane carboxylic acid 3-sulfo-NHS ester; Sulfo-SMCC | | amine | sulfhydryl | 9 | Used for protein conjugation; water soluble derivative |
| M 0155 | P-Maleimidopropionic acid NHS ester; BMPS | < | amine | sulfhydryl | 6 | Used for protein conjugation |
| M 5148 | N,N'-bis(3-Maleimidopropionyl)-2-hydroxy- 1,3-propanediamine | = | sulfhydryl | | 17 | Water soluble |
| P 0158 | 1,4-Phenylene diisothiocyanate | = | sulfhydryl | | 8 | |
| P 7518 | N,N'-o-Phenylenedimaleimide | = | sulfhydryl | | 8 | |
| P 3396 | N,N'-p-Phenylenedimaleimide | = | sulfhydryl | | 10 | |
| P 2672 | Polyoxyethylene bis(glycidyl ether); PEG bis(glycidyl ether) | = | amine or sulfhydryl | | >200 | Hydrophilic; oxirane requires basic pH to react |
| P 2050 | bis[Polyoxyethylene bis(glycidyl ether)] | = | amine or sulfhydryl | | >1000 | Hydrophilic; oxirane requires basic pH to react; contains 4 reactive groups |
| P 5532 | Polyoxyethylene bis(imidazolyl-carbonyl); PEG bis(CDI) | = | amine | | >200 | Hydrophilic |
| P 9532 | bis[Polyoxyethylene bis()imidozolyl-carbonyl)] | = | amine | | >1000 | Hydrophilc; contains 4 reactive groups |
| P 9299 | Polyoxyethylene bis(p-nitrophenyl carbonate); PEG bis(p-nitrophenyl carbonate) | = | amine | | >200 | Hydrophilic |
| P3415 | 3-(2-Pyridyldithio)propionic acid NHS ester; SPDP | < | amine | sulfhydryl | 4 | May undergo thiol/disulfide mter-change or be reduced to incorporate free sulfhydryl; used for protein conjugation |
| S 1885 | Suberic acid bis(NH ester) | = | amine | | 8 | | b. Indirect Examination of Protein:Protein Complexes
i. Double-Labeled Antibody In Situ Procedures by which labeled antibodies specific for target proteins are used in detection protein detection are well known in the art. In the present invention, double-labeling strategies, in which antibodies directed at each of a polyglutamine and a caspase are differentially labeled (e.g. with distinct fluorescent dyes, of which four, including 6-carboxy-fluorescein (FAM), tetrachloro-6-carboxyfluorescein (TET), 2,7-dimethoxy-4,5-dichloro-6-carboxyfluorescein (JOE) and hexachloro-6-carboxyfluorescein (HEX), are currently available), and extra- or intracellular co-localization of the two target proteins can be measured by confocal microscopy. Alternatively, immunological tests may rely on the use of either monoclonal or polyclonal antibodies and include enzyme-linked immunoassays (ELISA), immunoblotting and immunoprecipitation (see Voller, 1978, *Diagnostic Horizons*, 2: 1–7, Microbiological Associates Quarterly Publication, Walkersville, Md.; Voller et al., 1978, *J. Clin. Pathol.*, 31: 507–520; U.S. Reissue Pat. No. 31,006; UK Patent 2,019,408; Butler, 1981, *Methods Enzymol.*, 73: 482–523;; Maggio, E. (ed.), 1980, *Enzyme Immunoassay*, CRC Press, Boca Raton, Fla.) or radioinmunoassays (RIA) (Weintraub, B., *Principles of radioimmunoassays*, Seventh Training Course on Radioligand Assay Techniques, The Endocrine Society, March 1986, pp. 1–5, 46–49 and 68–78). For analyzing tissues for the presence or absence of a protein in the present invention, immunohistochemistry techniques may be used. Tissue samples to be assayed by these methods are prepared as described below. It will be apparent to one skilled in the art that the antibody molecule will have to labeled to facilitate easy detection of a target protein. Techniques for labeling antibody molecules are well known to those skilled in the art (see Harlour and Lane, 1989, *Antibodies*, Cold Spring Harbor Laboratory, pp. 1–726).

Alternatively, other techniques can be used to detect the target proteins, including chromatographic methods such as SDS PAGE, isoelectric focusing, Western blotting, HPLC and capillary electrophoresis. SDS-PAGE may be performed on cell lysates according to Weber and Osborn (1975, in: H. Neurath and R. Hill, eds., *The Proteins*, Ed. 3, Vol. I, Academic Press, New York, pp. 179–223, herein incorporated by reference) or immunoblots are performed according to Towbin et al (1979, *Proc. Natl. Acad. Sci. U.S.A.*, 76: 4350–4354). Primary anti-antibodies to many antigens may be obtained from commercial or other public sources (e.g. ATCC), or may be prepared by methods well known in the art. Secondary antibodies prepared against immunoglobulins of numerous species (including, but not limited to, rat, mouse, rabbit and goat) and suitable for use in a number of chromogenic, chemiluminescent and fluorescent detection protocols are commercially available (for example, from Promega, Madison, Wis.; Vector Laboratories, Burlingame, Calif.). Antibody dilution, incubations and detections are performed according to manufacturer's suggested conditions.

Preparation of Histological Samples

Tissue samples intended for use in in situ detection of either RNA or protein are fixed using conventional reagents; such samples may comprise whole or squashed cells, or may instead comprise sectioned tissue. Fixatives adequate for such procedures include, but are not limited to, formalin, 4% paraformaldehyde in an isotonic buffer, formaldehyde (each of which confers a measure of RNAase resistance to the nucleic acid molecules of the sample) or a multi-component fixative, such as FAAG (85% ethanol, 4% formaldehyde, 5% acetic acid, 1% EM grade glutaraldehyde). Note that for RNA detection, water used in the preparation of an aqueous component of a solution to which the tissue is exposed until it is embedded is RNAase-free, i.e. treated with 0.1% diethylprocarbonate (DEPC) at room temperature overnight and subsequently autoclaved for 1.5 to 2 hours. Tissue is fixed at 4° C., either on a sample roller or a rocking platform, for 12 to 48 hours in order to allow fixative to reach the center of the sample.

Prior to embedding, samples are purged of fixative and dehydrated; this is accomplished through a series of two- to ten-minute washes in increasingly high concentrations of ethanol, beginning at 60%—and ending with two washes in 95%—and another two in 100% ethanol, followed two ten-minute washes in xylene. Samples are embedded in one of a variety of sectioning supports, e.g. paraffin, plastic polymers or a mixed paraffin/polymer medium (e.g. Paraplast®Plus Tissue Embedding Medium, supplied by Oxford Labware). For example, fixed, dehydrated tissue is transferred from the second xylene wash to paraffin or a paraffin/polymer resin in the liquid-phase at about 58° C., then replace three to six times over a period of approximately three hours to dilute out residual xylene, followed by overnight incubation at 58° C. under a vacuum, in order to optimize infiltration of the embedding medium in to the tissue. The next day, following several more changes of medium at 20 minute to one hour intervals, also at 58 ° C., the tissue sample is positioned in a sectioning mold, the mold is surrounded by ice water and the medium is allowed to harden. Sections of 6 $\mu$m thickness are taken and affixed to 'subbed' slides, which are those coated with a proteinaceous substrate material, usually bovine serum albumin (BSA), to promote adhesion. Other methods of fixation and embedding are also applicable for use according to the methods of the invention; examples of these are found in Humason, G. L., 1979, *Animal Tissue Techniques,* 4th ed. (W. H. Freeman & Co., San Francisco), as is frozen sectioning (Serrano et al., 1989, supra).

ii. Fluorescence Energy Resonance Transfer (FRET)

A powerful tool with which to assess the distance between one molecule and another (whether protein or nucleic acid) or between two positions on the same molecule is provided by the technique of fluorescence energy resonance transfer (FRET), which now widely known in the art (for a review, see Matyus, 1992, *J. Photochem. Photobiol. B: Biol.,* 12: 323–337, which is herein incorporated by reference). FRET is a radiationless process in which energy is transferred from an excited donor molecule to an acceptor molecule; the efficiency of this transfer is dependent upon the distance between the donor an acceptor molecules. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range.

FRET may be performed either in vivo or in vitro. Proteins are labeled either in vivo or in vitro by methods known in the art. According to the invention, a caspase protein and a protein comprising a polyglutamine stretch are differentially labeled, one with a donor and the other with an acceptor moiety, and differences in fluorescence between a test assay, comprising a candidate inhibitor, and a control, in which the inhibitor is absent, are measured using a spectrophotometer, fluorimeter or laser-scanning microscope. The differential labels may comprise either a two different fluorophores (e.g., rhodamine, fluroescein isothiocyanate, SPQ, and others) or with a fluorophore and a molecule known to quench its signal; differences in the proximity of the caspase and the polyglutamine stretch with and without the candidate inhibitor can be gauged based upon a difference in the fluorescence spectrum or intensity observed.

A sample, whether in vitro or in vivo, assayed according to the invention therefore comprises a mixture at equilibrium of labeled proteins which, when disassociated from one another, fluoresce at one frequency and, when complexed together, fluoresce at another frequency or, alternatively, of molecules which either do or do not fluoresce depending upon whether or not they are associated. In the former case, a shift from one frequency to the other of at least 30% of labeled molecules in the screening assay in the presence of the inhibitor relative to that observed in controls in which it is absent, indicates effective inhibition according to the invention. Likewise in the latter case, a difference in total fluoresence between test and control FRET analyses indicates that the candidate inhibitor is an effective inhibitor of cell death according to the invention.

iii. A technique, the "two-hybrid" system, for monitoring protein:protein interactions in vivo has been developed in the yeast system for the isolation of protein binding partners. Typically, chimeric proteins are produced in which a protein for which partners are to be found (the "bait") is fused to the DNA-binding domain of monomeric half of a heterodimeric transcription factor, while a library of potential binding partners are fused to the DNA-binding domain of the second half of that same heterodimer. If plasmids encoding the bait and a protein which will bind it are present in the same cell, a functional transcription complex is formed and a marker gene under control of a regulatory element specific for that complex is expressed. Such gene expression constructs may be made for use in the invention in which one plasmid encodes a fusion between caspase and one DNA-binding protein while the other encodes either polyglutamine or an adaptor protein through which caspase associates with polyglutamine fused to a second DNA-binding protein. Either plasmid carries a different selectable marker (e.g., an auxotrophic marker), as described above along with useful yeast plasmids. Optionally, an additional plasmid may encode a similar fusion construct comprising an adaptor protein.

According to the invention, the assay would be performed in the presence of a candidate inhibitor of cell death; control reactions would be performed without the inhibitor. An inhibitor may be delivered to the cells on a third yeast plasmid, which is maintained using a third selective marker, or may be present in the culture medium from which it is taken up by the cells.

A decrease of at least 30% in marker gene in the presence of the candidate inhibitor of transcription relative to that observed in controls in which it is absent indicates effective inhibition.

c. Monitoring of Cell Death/Survival

According to the methods of the invention, screening assays may be performed in which treated and untreated samples comprising cells may be examined for the rate of cell death.

i. Cell Counting

In an in vivo assay system, gross quantitation of cell survival may be made by visual comparison of tissue slices (prepared as described above) obtained from test and control animals for areas of cell loss; the percent reduction in the amount of tissue loss in organisms treated with a candidate inhibitor according to the invention relative to untreated controls can be quantitated.

In an in vitro cell-based assay system of the invention, live cells (as judged by morphological criteria) may be counted, e.g. using a hemocytometer, in diluted samples drawn from test and control cultures. Alternatively, after administration of the candidate inhibitor according to the invention, test and control cultures may be diluted in fresh media and serially cultured. In this case, colony-forming-units (directly proportional to the number of live cells in a culture) are counted and the numbers compared between treated and untreated cultures.

An increase in the number of viable cells in cultures or organisms treated with a candidate inhibitor of the invention of 30% or more relative to that observed in untreated control cultures indicates that a candidate inhibitor is an effective inhibitor of cell death according to the invention.

ii. Histological Examination

Cell viability may be measured by any of a number of histological criteria. For example, morphological features (e.g., rounding up and detachment from a substrate material of cells which are normally flat and attached, inflation/bursting of membrane-limited structures, such as the nucleus or mitochondria, or membrane "blebbing") are useful; however, a more sensitive and objective assay of the entry of cells into a cell-death program may be performed. This assay, which comprises a method of TdT-mediated dUTP-biotin nick end labeling (TUNEL; Gavrieli et al., 1992 *J. Cell Biol.*, 119: 493–501), detects chromosomal DNA breakage such as occurs during apoptosis. It allows monitoring of both the distribution and numbers of cells undergoing programmed death and quantitation of the process as it occurs. The procedure, as it is applied to fixed, sectioned tissue samples, may be summarized briefly as follows:

Tissue samples are fixed in 4% buffered formaldehyde and embedded in paraffin. 4–6 μm paraffin sections are adhered to slides pretreated with a 0.01% aqueous solution of poly-L-lysine (300,000 M. W.; Sigma Chemical Co., St. Louis, Mo.). Deparaffinization is done by heating the sections for 10 minutes at 70° C., or 30 minutes at 60° C. Hydration is done by transferring the slides through the following solutions: twice in xylene (5 minutes each), and (3 minutes each): twice in 96% ethanol, 90% ethanol, 80% ethanol, and double-distilled water (DDW). Fresh solvents are recommended as traces might interfere with the enzymatic reaction.

Nuclei of tissue sections are then stripped of proteins by incubation with 20 μg/ml proteinase K (PK) (Sigma Chemical Co.). For 15 minutes at room temperature, and the slides are then washed in DDW for 2 min, four times. Endogenous peroxidase is inactivated by covering the sections with 2% $H_2O_2$ for 5 minutes at room temperature. The sections are rinsed with DDW and immersed in TDT buffer (30 mM Trizma base, pH 7.2, 140 mM sodium cacodylate, 1 mM cobalt chloride). TDT (0.3 e.u./μl) and biotinylated dUTP in TDT buffer are then added to cover the sections, and then incubated in a humid atmosphere at 37° C. for 60 minutes. The reaction is terminated by transferring the slides to TB buffer (300 mM sodium chloride, 30 mM sodium citrate) for 15 minutes at room temperature. The sections are rinsed with DDW, covered with 2% aqueous solution of human serum albumin (HSA), or BSA for 10 minutes at room temperature, rinsed in DDW, and immersed in PBS for 5 minutes. The sections are covered with Extra-avidin Peroxidase (BioMakor; Rehovot, Israel) diluted 1:10–1:20 in water, incubated for 30 minutes at 37° C., washed in DDW, immersed for 5 minutes in PBS, and stained with AEC for about 30 minutes at 37° C.

Staining is then observed microscopically. An adaptation of the above procedure for dissociated cells is also described (Gavrieli et al., 1992, supra).

A decrease in detected signal resulting from end-labeled DNA of at least 30% in test samples comprising the inhibitor relative to control samples in which it is absent is indicative of effective inhibition of cell death according to the invention.

Other histological techniques, such as conventional staining protocols or in situ hybridization techniques with labeled antibodies (to detect protein complexes) or nucleic acid probes (to detect mnRNAs of interest) may be performed as is generally described above. A similar standard for the determination of efficacy as is described in the above procedures holds when one of these several screening assays is performed.

d. Monitoring of Phenotypic Changes

As stated above, when assaying an inhibitor of cell death in the invention, it is possible to examine its effect on cell survival or structural characteristics; however, in a multicellular organism (including, but not limited to, an insect or vertebrates, particularly a mammal), it is additionally possible to determine the efficacy of a candidate inhibitor by measuring other parameters. As the invention is particularly suited to the screening of agents which may inhibit neuronal cell death, one may quantify such changes in such parameters as strength, motor control or cognitive function, for which tests are well known in the art in both insect and mammalian model systems. In Drosophila, suitable tests include the fast-phototaxis assay (in which the normal tendency of flies to gravitate toward a light source is quantified) and various chemoattraction assays are known for behavioral testing, while motor function is tested in a separate assay measuring the height and speed with which the test and control animals are able to jump. In the mouse system, classic tests of cognitive function include the maze and submerged platform tests, in which the test animal is required to learn and/or remember a route or location. Simple comparison of test animals treated with a candidate inhibitor according to the invention with untreated control animals for the ability to walk or perform other motor functions may be performed; it is well within the knowledge of one of skill in the biological or medical art to determine when functional improvement has occurred in response to treatment with the candidate inhibitor. Where the results can be quantified numerically, an improvement in cognition or motor function of at least 30% should be observed in order for a candidate inhibitor to be judged effective according to the invention.

e. Determination of Activity of an Inhibitor of Cell Death

A candidate inhibitor of cell death, assayed according to the invention as described above, is determined to be effective if its use results in a difference of about 30% or greater relative to a control in which it is not present in indices such as the amount recovered or detected of a protein complex comprising a caspase and a protein comprising a polyglutamine stretch, the presence or extent of histological or molecular indicators associated with death programs (e.g. membrane abnormalities or chromosomal degradation, as described above), changes in clinical indicators such as motor or cognitive function, or in the rate of cell death.

The level of inhibition by a candidate inhibitor may be quantified using any acceptable limits, for example, via the following formula:

$$\text{Percent Modulation} = \frac{(Index_{Control} - Index_{Sample})}{(Index_{Control})} \times 100$$

where $Index_{Control}$ is the quantitative result obtained in assays that lack the candidate inhibitor (in other words, untreated controls), and Index$_{Sample}$ represents the result of the same measurement in assays containing the candidate inhibitor.

C. Dosage and Administration of a Candidate Inhibitor According to the Invention i. Dosage When the amount of a a protein or other candidate inhibitor to be administered to a test cell or animal is considered, it will be apparent to those of skill in the art that the therapeutically-effective amount of a composition administered in the invention will depend, inter alia, upon the efficiency of cellular uptake of a composition, the administration schedule, the unit dose administered, whether the compositions are administered in combination with other therapeutic agents, the health of the recipient, and the therapeutic activity of the particular protein or other pharmaceutical substance.

The precise amount of a protein or other pharmaceutical agent identified according to the invention and required to be administered depends on the judgment of one of skill in the art and may be peculiar to each subject, within a limited range of values. The amount of inhibitor will typically be in the range of about 1 ug–100 mg/kg body weight. Where the modulator is a peptide or polypeptide, it is typically administered in the range of about 100–500 ug/ml per dose. A single dose of a candidate inhibitor, or multiple doses of such a substance, daily, weekly, or intermittently, is contemplated according to the invention.

A candidate inhibitor is tested in a concentration range that depends upon the molecular weight of the molecule and the type of assay. For example, for inhibition of protein/protein or protein/DNA complex formation or transcription initiation, small molecules (as defined above) may be tested in a concentration range of 1 pg–100 $\mu$g/ml, preferably at about 100 pg–10 ng/ml; large molecules, e.g., peptides, may be tested in the range of 10 ng–100 $\mu$g/ml, preferably 100 ng–10 $\mu$g/ml.

Generally, nucleic acid molecules are administered in a manner compatible with the dosage formulation, and in such amount as will be prophylactically and/or therapeutically effective. When the end product (e.g. an antisense RNA molecule or ribozyme) is administered directly, the dosage to be administered is directly proportional to the the amount needed per cell and the number of cells to be transfected, with a correction factor for the efficiency of uptake of the molecules. In cases in which a gene must be expressed from the nucleic acid molecules, the strength of the associated transcriptional regulatory sequences also must be considered in calculating the number of nucleic acid molecules per target cell that will result in adequate levels of the encoded product. Suitable dosage ranges are on the order of, where a gene expression construct is administered, 0.5- to 1 $\mu$g, or 1–10 $\mu$g, or optionally 10–100 $\mu$g of nucleic acid in a single dose. It is conceivable that dosages of up to 1 mg may be advantageously used. Note that the number of molar equivalents per cell vary with the size of the construct, and that absolute amounts of DNA used should be adjusted accordingly to ensure adequate gene copy number when large constructs are injected.

If no effect is seen within four orders of magnitude in either direction of the starting dosage, it is likely that the agent is not of use according to the invention. It is critical to note that when high dosages are used, the concentration must be kept below harmful levels, which may be known if a candidate inhibitor is a drug that is approved for clinical use. Such a dosage should be one (or, preferably, two or more) orders of magnitude below the LD$_{50}$ value that is known for a laboratory mammal, and preferably below concentrations that are documented as producing serious, if non-lethal, side effects. If it determined that a candidate inhibitor is optimally useful at levels that are harmful if achieved systemically, that agent should be used for local administration only, and then only at such doses where diffusion of the drug from the target site reduces its concentration to safe levels.

ii. Administration

Candidate inhibitors which are screened according to the invention may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Administration of a candidate inhibitor as described herein may be either localized or systemic.

Localized Adminstration

It is contemplated that global administration of a candidate inhibitor to an animal is not needed in order to achieve a highly localized effect. Localized administration of a nucleic acid is preferably by via injection or by means of a drip device, drug pump or drug-saturated solid matrix from which the nucleic acid can diffuse implanted at the target site. When a tissue that is the target of treatment according to the invention is on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Compositions comprising a therapeutic composition which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) An liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

In a specialized instance, the tissue to which a therapeutic composition is the lung. In such a case the route of administration is via inhalation, either of a liquid aerosol or of a nebulized powder of. Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin. Invest.*, 84: 1349–1354).

Systemic Administration

Systemic administration of a nucleic acid or other therapeutic composition according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced nucleic acid or other material or may, instead, comprise cells that produce and secrete a candidate inhibitor. Note that injection may be performed either by conventional means (i.e. using a hypodermic needle) or by hypospray (see Clarke and Woodland, 1975, *Rheumatol. Rehabil.,* 14: 47–49).

Systemic administration is advantageous when a pharmaceutical composition must be delivered to a target tissue that is widely-dispersed, inaccessible to direct contact or, while accessible to topical or other localized application, is resident in an environment (such as the digestive tract) wherein the native activity of the nucleic acid or other agent might be compromised, e.g. by digestive enzymes or extremes of pH.

Candidate inhibitors to be screened according to the invention can be given in a single- or multiple dose. A multiple dose schedule is one in which a primary course of administration can include 1–10 separate doses, followed by other doses given at subsequent time intervals required to maintain and or reinforce the cellular level of the transfected nucleic acid. Such intervals are dependent on the continued need of the recipient for the candidate inhibitor; in the case of a nucleic acid molecule, its ability to self-replicate in a test cell if it does not become integrated into the recipient's genome and the half-life of a non-renewable nucleic acid (e.g. a molecule that will not self-replicate) are important factors to consider.

Nucleic acid or protein molecules to be administered according to the invention also may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Administration of a nucleic acid molecule as described herein may be either localized or systemic. Delivery of a nucleic acid may be performed using a delivery technique selected from the group that includes, but is not limited to, the use of viral vectors and non-viral vectors, such as episomal vectors, artificial chromosomes, liposomes, cationic peptides, tissue-specific cell transfection and transplantation, administration of genes in general vectors with tissue-specific promoters, etc.

EXAMPLE 1

The methods and reagents employed in the experiments described in Examples 1 and 2, may be briefly summarized as follows:

Transient transfections and viability assays: Cultured cells present at a density of $2 \times 10^4$ per 35 mm tissue-culture well were transfected by calcium phosphate precipitation with 1 μg of CMX-Q79 construct and and 0.2 μg of pEGFPNI DNA as a tracer. In co-transfection experiments, pcDNA-AU1-FADDN was used in a 5:1 ratio to the CMX-Q-79 construct. Apoptotic cells were identified by visual inspection of GFP-positive cells using a Nikon inverted microscope. Fluorescent cells exhibiting membrane blebbing were scored as apoptotic. Each experiment was done in duplicate with over 100 cells counted for each determination.

Cell lines and Primary Neuronal cultures: Cell lines (Hela, NT2, 3T3, EF, MCF7 and 293T) were seeded at $2 \times 10^4$ cells per 35 mm well in DMEM medium (Gibco) containing 10% fetal calf serum (FCS). Neurons of the striatum, cerebellum, hippocampus and cerebral cortex were obtained from E17 rat embryos (Taconic) and cultured in neurobasal medium containing B27 supplement (Gibco), as previously described. Primary neurons were plated at $1 \times 10^5$ cells/well in six-well plates. At div4, neurons were transfected by calcium phosphate method (Dudek et al., 1997, *Science,* 275: 661–664) for 3 hours.

Plasmids and reagents: The haemagglutinin-tagged 5' end of the ataxin-3 gene containing 79 or 26 polyglutamine repeats was cloned into a CMX vector (CMX-79 and CMX-26; Ikeda et al., 1996, supra). The CMX-79 plasmid was subcloned into the EcoR1-Xho1 fragment of the pEG-FPN1 vector (Clontech). The plasmids pcDNA-AU1-FADDN, pcDNA3-AU1-FADD, and pcDNACaspase8C360S (Chinnaiyan et al., 1995, supra; Chinnaiyan et al., 1996, supra) as well as pcDNABcl-x, pcDNABcl-2 and the PhD crm-a 1.2 expresssion vector (Gagliardini et al., 1994, *Science,* 263: 826–828 [published erratum appears in *Science,* 1994, 264(5164): 1388]) were used. Plasmids for transfections were prepared using a commercial maxi-prep kit (Qiagen).

Antibodies against human FasL (NOK-1), cytochrome c, and FADD were obtained from Pharmigen (catalog #'s 65320C, 65971A and 65751A, respectively). Anti-Caspase 3 antibody (Signal Transduction Laboratories). zVad-FMK and DEVD-CHO were obtained from Kamiya Biochemical Co. HeLa, NT2, and MCF7 cells were obtained from ATCC. Embryonic fibroblast cells were from knockout mice deficient for caspase 11, caspase 2, and caspase 1 (Wang et al., 1998, *Cell,* 92: 501–509; Bergerone et al., 1998, *Genes Dev.,* 12: 1304–1314).

Immunofluorescence and Confocal Microscopy. Hela cells were grown in lab tek slide culture chambers at a density of $2 \times 10^3$ cells per chamber. Twenty-four hours after transfection, cells were fixed with cold acetone for 10 minutes. Slides were washed with two changes of phosphate-buffered saline (PBS; 137 mM NaCl, 2.7 mM KCl, 5.3 mM $Na2HPO_4 \cdot H_2O$ and 1.4 mM $KH_2PO_4$) and incubated with blocking medium containing 5% fetal calf serum (FCS), 0.1% Triton X-100 in PBS for 20 min. Primary antibodies diluted in 1% FCS, 0.1% triton in PBS were added for 2 hours, and incubated with secondary antibody for 30 minutes. Slides were washed with PBS three times between and after antibody incubations, incubated with Hoechst 33342 for 10 min, and mounted in PBS containing 90% glycerol and 10 mg/ml phenylamine. In some experiments, mitochondria were labeled by incubating cells for 20 minutes at 37° C. with 10 nm Mitotracker™ Red (Molecular Probes, catalog # R7512). Primary antibodies included the anti-HA 11.1 and AU1 monoclonal antibodies (Babco). Slides were examined using a Zeiss Axiophot inverted confocal microscope.

Cell fractionation and Western blotting: $1 \times 10^6$ cells/ml were transfected in 10 cm dishes with the constructs as indicated above. Twenty eight hours after transfection, cells were rinsed in PBS and lysed at 40° C. in RIPA (150 mM NaCl, 1% Nonidet NP-40, 0.1% SDS and 50 mM Tris, pH 8.0) buffer in the absence of deoxycholate. After centrifugation at 15,000×g at 4° C., the insoluble (pellet) and soluble (supernatant) fractions were separated. In some experiments, the insoluble and soluble fractions were separated by centrifugation at 14,000 g for 10 minutes.

Determination of the Mechanism of Polyglutamine-Induced Cell Death

To determine the mechanism by which polyglutamine inclusions induce cell death, a transient transfection system expressing various versions of ataxin-3 was established. The expression of a truncated ataxin-3 containing 79 glutamine repeats (named Q79) was sufficient to induce apoptosis in HeLa cells (FIG. 1A); however, this effect was not observed when either a truncated ataxin-3 containing 35 glutamine repeats or a full-length ataxin-3 containing either 79 or 35 glutamine repeats was assayed (not shown). To determine whether caspases play a role in polyglutamine-induced cell death, crmA (a cowpox virus gene encoding a serpin that is a specific inhibitor of caspases) was co-transfected with a nucleic acid construct expressing Q79, resulting in inhibition of Q79-induced cell death (FIGS. 1A and 1B). The effect of crmA on the formation of polyglutamine inclusions was examined by expressing a Green Fluorescent Protein (GFP)-tagged Q79 expression construct with the crmA expression construct and counting the numbers of inclusions per transfected cell in the presence or absence of crmA (80% vs. 85%). The results indicated that although the presence of CrmA inhibited Q79-induced cell death, it did not affect the formation of polyglutamine inclusions.

Experiments were performed to determine the involvement, if any, of caspases in polyglutamine inclusion-induced cell death. In vitro kinetic analyses revealed that CrmA has the most potent effect on caspase-1 followed by caspase-8; its effects on other caspases (such as caspases 3, 6 and 7) are weaker by several orders of magnitude, making them irrelevant as physiological targets for CrmA. To determine the role of caspase-l in polyglutamine inclusion-induced cell death, the Q79 expression construct was transfected into mouse embryonic fibroblasts lacking caspase-1 (casp-1 homozygous null EF cells) and found that casp-1 homozygous null EF cells are susceptible to cell death induced by Q79 (37% of WT EF cells died, while 40% of casp-1 EF cells died), indicating that caspase-1 is not required for polyglutamine-induced cell death.

Caspase-8 and the Fas pathway were examined to determine whether either plays a role in mediating cell death induced by polyglutamine inclusions. FADD ΔN, an inhibitor of the Fas pathway of apoptosis, was co-transfected with Q79 and the effect of FADD ΔN on Q79-induced cell death determined. In this experiment, FADD ΔN efficiently inhibited cell death induced by Q79, suggesting that mediators of the Fas pathway might be involved (FIGS. 1A and 1B). To examine the involvement of the extracellular signalling of the Fas pathway, the ability of a Fas ligand neutralizing antibody to inhibit Q79-induced cell death was assayed. A Fas ligand neutralizing antibody, (NOK-1, Pharmigen) had no effect on Q79-induced cell death when used at 0.5 μg/ml to 1.0 μg/ml, twice the concentration previously reported to inhibit Fas-induced cell death, suggesting that the extracellular signalling component of the Fas pathway is not involved in mediating cell death induced by polyglutamine inclusions. To determine the mechanism by which FADD ΔN inhibits Q79-induced cell death, the subcellular localization of FADD ΔN was examined in the presence and absence of Q79 expression. Consistent with the report by (Perez and White, 1998, *J. Cell Biol.*, 141: 1255–1266),we found that a GFP-tagged FADD ΔN was diffusely distributed in the cytoplasm and nucleus and present mostly in the soluble fraction (FIG. 2). Coexpression of FADD ΔN with Q79, however, resulted in the recruitment of FADD ΔN into Q79 inclusions and moved FADD ΔN from the soluble fraction into the insoluble fraction (FIG. 2). While not being bound by any theory or hypothesis, these results suggest that the polyglutamine inclusions are able to recruit FADD ΔN through interaction with the death domain of FADD and that such interactions may inhibit the recruitment of cell death-inducing proteins.

To determine whether protection from polyglutamine inclusion-induced cell death can be extended to primary neurons, a culture system for mouse cerebellar neurons was established. Cerebellar neurons were isolated from E17 rat embryos and cultured in serum-free medium as previously described (Brewer et al., 1995, *J. Neurosci. Res.*, 42: 674–683) to establish a culture consisting primarily of cerebellar neurons of which a high proportion were purkinje cells. Expression of Q79 induced over 40% of purkinje cells to die in 2 days (FIG. 2).

To determine the mechanism by which FADD ΔN inhibits Q79-induced cell death, the subcellular localization of FADD ΔN was determined in the presence of absence of Q79 expression. The results indicate that FADD ΔN is normally present in the soluble fraction and that expression of Q79 moves FADD ΔN from the soluble to the insoluble fraction and results in aggregate formation (FIG. 3).

The expression level and distribution of endogenous caspase-8 was analyzed in cells transfected with Q79. Since Q79 forms insoluble inclusions, the presence of caspase-8 was assessed in soluble and insoluble fractions of control cells, cells expressing Q79 and cells expressing the following combinations of proteins:

Q79 and crmA,

Q79 and FADD ΔN,

Q79 and bcl-2, and

Q79 and N-terminally tagged Bcl-xL.

Caspase-8 was detected in the soluble fraction of control cells as well as cells coexpressing Q79 and crmA, Q79 and FADD ΔN, Q79 and bcl-2; caspase-8 was instead detected in the insoluble fractions of cells expressing Q79 alone and of cells expressing Q79 and Bcl-xL (FIG. 4). These results suggest that Q79 recruits caspase-8 into the insoluble fraction and that the inhibition of Q79-induced cell death is correlated with the prevention of such recruitment.

To obtain evidence that Q79 inclusions can recruit caspase-8, the intracellular expression patterns of a C360S caspase-8 mutant were examined in the presence or absence of Q79 expression. The C360S protein carries an inactivating mutation at $Cys_{360}$, which is at the reaction center of the molecule; it was necessary to use a disabled caspase-8 protein, as the wild-type protein would prove lethal to the test cells if expressed at detectable levels. Transfection of low levels (0.3 μg/well in a 6-well plate) of a GFP-tagged mutant caspase-8 resulted in an even intracellular distribution of caspase-8. When co-expressed with GFP-tagged Q79, a mutant caspase-8 tagged with haemagluttinin (HA) was found to be recruited into polyglutamine inclusions (FIG. 4).

Detection of Caspase-8-Like Immunoreactivity in the Insoluble Fractions of HD Caudate Samples To determine if recruitment of caspase-8 can be detected in postmorten patient brain samples of polyglutamine expansion diseases, the distribution of caspase-8 was examined by Western analysis in human HD patient caudate samples as well as in control brain samples. In ⅘ caudate samples from Huntington's patients, a band reactive with an anti-caspase monoclonal antibody was detected; this band was not observed in any of the three samples obtained from caudate samples drawn from neurologically unremarkable subjects. The detected band, which indicated a protein of approximately 46 kD, reacted specifically with the anti-caspase-8 monoclonal antibody in the insoluble fraction; the detected protein is the same molecular weight as the activated caspase-8 in the staurosporin-treated HeLa cell lysates (FIG. 5). In addition, the level of caspase-8 immunoreactivity was found to be much higher in HD caudates than that of control. This result suggests not only that elevated levels of caspase-8 are recruited into the insoluble fraction, but also that this protein is activated in HD caudate samples. Since the sequence identity of the 46 kD band in HD caudates has not been determined, it is also possible that a protein immunologically related to caspase-8, present in much lower levels in the control brains, may have been recruited into the insoluble fraction in HD caudates.

These results provide the first demonstration that polyglutamine inclusions can specifically recruit caspase-8 and that such recruitment is critically important for polyglutamine-induced cell death.

EXAMPLE 2

Screening of Inhibitors of Cell Death According to the Invention

Since expression of Bcl-2 and Bcl-xL have been shown to inhibit apoptosis in a variety of systems, we examined if expression of Bcl-2 and Bcl-xL can inhibit cell death induced by Q79, we found that expression of Bcl-2, but not N-terminally tagged Bcl-xL, inhibits cell death induced by Q79 (FIGS. 1A and 1B).

To determine whether crmA, FADD ΔN and Bcl-2 could inhibit caspase-8 recruitment, a GFP-tagged mutant caspase-8, an HA-tagged Q79 and one of the candidate inhibitors, crmA, FADD ΔN, or Bcl-2 were co-expressed in HeLa cells. The results indicated that co-expression of crmA, FADD ΔN and Bcl-2 can indeed inhibit the recruitment of caspase-8 into Q79 inclusions (FIG. 4). These results suggest that the recruitment of caspase-8 is critically important for cell death induced by polyglutamine repeats.

The results obtained in HeLa cells indicated that coexpression of crmA, bcl-2, FADD ΔN, but not N-terminally tagged Bcl-xL, inhibited cell death induced by Q79. To further examine the mechanism of Q79-induced cell death, cultures of mouse primary striatal and cortical neurons were established. While expression of Q79 resulted in the death of 30–40% of primary striatal and cortical neurons within 2 days, coexpression of crmA and FADD ΔN insignificantly (5–10%) inhibited cell death induced by Q79 (FIG. 2B). These results suggest that Q79 induces the death of HeLa cells and of mouse cerebellar, striatal and cortical neurons in primary culture through a similar mechanism, which mechanism can be inhibited by crmA and FADD ΔN. Interestingly, coexpression of crmA, bcl-2 and FADD ΔN not only prevented the cell death induced by Q79 but also resulted in extensive preservation of neurites (FIG. 2C). This is in contrast with the inhibition of neuronal cell death induced by trophic factor deprivation, wherein although crmA and bcl-2 can suppress neuronal cell death, they cannot prevent the loss of neurites (Allsopp et al., 1993, C1, 73: 295–307; Gagliardini et al., 1994, supra). These results suggest that crmA, bcl-2 and FADD ΔN may be able not only to prevent polyglutamine-induced cell death, but also to maintain neuronal function.

These results represent the first discovery of inhibitors of polyglutamine-induced cell death. In this example, it has been determined that two inhibitors of caspase-8 recruitment, CrmA and FADD ΔN, act by distinct mechanisms. While not being bound by any theory, since CrmA is a pseudo-substrate type of inhibitors and inhibits caspases by forming a tight complex (Komiyama et al., 1994), it is likely that CrmA interacts directly with caspase-8. FADD ΔN, on the other hand, is likely to interact directly with polyglutamine inclusions and thereby prevent the recruitment of caspase-8. FADD ΔN consists of mostly a death domain which interacts homophilically with the death domain of Fas receptor in the Fas pathway of apoptosis. The results presented in this Example suggest that the death domain can also interact with the polyglutamine inclusions. Although it is not yet clear how caspase-8 is recruited to the polyglutamine inclusions, it is possible that an adaptor protein, which consists of a death domain and two death effector domains, may act as a bridge between the polyglutamine repeats and caspase-8. FADD is an example of one such protein.

EXAMPLE 3

Cell Death After Induction of Expanded Polyglutamine Repeat

FIG. 6 shows polyglutamine-induced cell death after induction of expanded polyglutamine-repeat, and FIG. 7 shows results of in vitro binding assays of expanded polyglutamine repeats.

EXAMPLE 4

A Kit for Screening Candidate Inhibitors of Cell Death According to the Invention In order to facilitate convenient and widespread use of the invention, a kit is provided which contains the essential components for screening for inhibitors of polyglutamine-induced cell death. A caspase, selected from the group that includes caspases 1 through 12 as well as proteins comprising a caspase sequence (such as, but not limited to, FLIP and FLICE) is provided, as is a polyglutamine. These components are, independent of each other, provided as a protein or a nucleic acid comprising a gene expression construct encoding the protein, and are either in solution (preferably refrigerated or frozen) in a buffer which inhibits degradation and maintains biological activity, or are provided in dried form, i.e., lyophilized. In the latter case, the components are resuspended prior to use in a buffer which, if the components are proteinaceous, permits protein:protein interaction and, if the components are nucleic acids, permits either transfection/transformation into a cell or organism or in vitro transcription/translation, as described above. The kit optionally comprises an adaptor protein, provided in similar manner as the caspase and polyglutamine. Each of these components is supplied separately contained or in admixture with one or more of the others in a container selected from the group that includes, but is not limited to, a tube, vial, syringe or bottle.

Optionally, the kit includes cells. Eukaryotic or prokaryotic cells, as described above, are supplied in—or on a liquid or solid physiological buffer or culture medium (e.g. in suspension, in a stab culture or on a culture plate, e.g. a Petri dish). For ease of shipping, the cells are typically refrigerated, frozen or lyophilized in a bottle, tube or vial. Methods of cell preservation are widely known in the art; suitable buffers and media are widely known in the art, and are obtained from commercial suppliers (e.g., Gibco/LifeTechnologies) or made by standard methods (see, for example Sambrook et al., 1989, *Molecular Cloning, A Laboratory Manual.*, 2nd Edition, Cold Spring Harbor Laboratory Press, Cold Spring Harbor, N.Y.).

An assay of the invention is carried out using the kit according to the methods described above in Example 2 and elsewhere.

The invention is useful in providing a means by which candidate inhibitors of cell death, may be screened for efficacy. In particular, the invention is useful in identifying therapeutic molecules for the treatment of degenerative diseases, such as neurodegenerative diseases or other diseases characterized by polyglutamine-induced cell death. Consequently, the invention additionally is useful in determining the appropriate dosage and means of administration for a therapeutic composition so identified. The invention is further useful, in that it provides a kit comprising the essential reagents for such an assay, enabling the widespread use of the methods of the invention, thereby increasing the convenience with which candidate inhibitors of cell death may be screened and the frequency with which compositions effective in inhibiting cell death are identified.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method for identifying an inhibitor of cell death comprising
   (a) incubating a first protein comprising a caspase, a protein fragment comprising a polyglutamine stretch and a candidate inhibitor of cell death under conditions sufficient to permit formation of a complex,
   (b) comparing formation of the complex to complex formation in the absence of said candidate inhibitor whereby reduction in the formation of the complex indicates that said candidate inhibitor is an inhibitor of cell death.

2. The method according to claim 1, wherein said protein comprising a caspase is selected from the group consisting of caspases 1, 2, 3, 4, 5, 6, 7, 8, 9, 10, 11 and 12.

3. The method according to claim 1, wherein said polyglutamine stretch is glutamine$_{79}$ (Q79).

4. The method according to claim 1, wherein in step (a) an adaptor protein is incubated with said first protein and said protein fragment.

5. The method according to claim 4, wherein said adaptor protein comprises a death domain (DD) and one of a death effector domain (DED) and a caspase-recruitment domain (CASP).

6. The method according to claim 4, wherein said adaptor protein is FADD.

7. The method according to claim 1, wherein step (b) includes isolating the complex.

8. The method according to claim 1, wherein step (b) includes observing the complex by fluorescent resonance energy transfer (FRET).

9. The method according to claim 1, wherein step (b) includes using a multiple-hybrid reporter system in yeast.

10. The method according to claim 1, wherein step (b) includes histological examination of cells for signs of said cell death.

11. The method according to claim 10, wherein said signs are selected from the group consisting of inflation of the nucleus or mitochondria, degradation of chromosomal DNA and rupture of one or more of the nuclear, plasma and mitochondrial membranes.

12. The method according to claim 1, wherein step (b) includes measuring survival rate of cells in vivo.

13. The method according to claim 1, wherein step (b) includes measuring the survival rate of cells in vitro.

14. The method according to claim 13, wherein said cells in vitro are selected from the group consisting of mammalian cells and yeast.

15. The method according to claim 14, wherein said mammalian cells are neuronal.

16. The method according to claim 13, wherein said cells in vitro comprise one or more of a nucleic acid encoding said first protein, a nucleic acid encoding said protein fragment and a nucleic acid encoding said candidate inhibitor.

17. A kit for identifying an inhibitor of cell death, comprising a protein comprising a caspase, a protein fragment comprising a polyglutamine stretch and packaging therefor.

18. The kit of claim 17, wherein said kit further comprises an adaptor protein.

19. The kit of claim 18, wherein said adaptor protein comprises a death domain (DD) and one of a death effector domain (DED) and a caspase-recruitment domain (CASP).

20. The kit of claim 18, wherein said adaptor is FADD.

21. The kit of claim 17, wherein said kit further comprises cells.

22. The kit of claim 21, wherein said cells are selected from the group consisting of mammalian cells and yeast.

23. The kit of claim 21, wherein said cells contain one or more of a nucleic acid encoding said first protein, a nucleic acid encoding said protein fragment and a nucleic acid encoding a candidate inhibitor of cell death.

* * * * *